United States Patent
Chandrasekaran et al.

(10) Patent No.: US 12,103,935 B2
(45) Date of Patent: Oct. 1, 2024

(54) SECO-AMBRAKETALS

(71) Applicant: SYMRISE AG, Holzminden (DE)

(72) Inventors: Vijayanand Chandrasekaran, Holzminden (DE); Bernd Hölscher, Halle (DE); Janis Blume, Beverungen (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 18/245,266

(22) PCT Filed: Sep. 18, 2020

(86) PCT No.: PCT/EP2020/076164
§ 371 (c)(1),
(2) Date: Mar. 14, 2023

(87) PCT Pub. No.: WO2022/058021
PCT Pub. Date: Mar. 24, 2022

(65) Prior Publication Data
US 2023/0348488 A1     Nov. 2, 2023

(51) Int. Cl.
*C07D 493/08*     (2006.01)
*A61K 8/49*     (2006.01)
*A61Q 13/00*     (2006.01)

(52) U.S. Cl.
CPC .......... *C07D 493/08* (2013.01); *A61K 8/4973* (2013.01); *A61Q 13/00* (2013.01)

(58) Field of Classification Search
None
See application file for complete search history.

(56) References Cited

FOREIGN PATENT DOCUMENTS

| WO | 2015036402 A1 | 3/2015 | |
|---|---|---|---|
| WO | WO-2016097569 A1 * | 6/2016 | ............... A61K 8/49 |
| WO | 2018233804 A1 | 12/2018 | |

OTHER PUBLICATIONS

Muratore et al., WO 2016097569 Machine Translation, Jun. 23, 2016 (Year: 2016).*
International Search Report and Written Opinion issued on Apr. 9, 2021 for corresponding PCT Application No. PCT/EP2020/076164.
Evans, Gary B. et al.; "Convenient syntheses of ring-B-nor analogues of Ambrox and amberketal via a novel ring contraction reaction," Tetrahedron Letters, vol. 55, No. 45, 2014, pp. 6227-6230 XP029080072.

* cited by examiner

*Primary Examiner* — Jessica Whiteley
(74) *Attorney, Agent, or Firm* — POLSINELLI PC

(57) ABSTRACT

The present invention primarily relates to compounds of formula (I) and compositions comprising one, two, three or more compound(s) of formula (I) or consisting of two, three or more compound(s) of formula (I). The invention further relates to methods for producing a compound of formula (I) or a composition as defined herein, the use of a compound of formula (I) as defined herein as a fragrance substance, the use of a composition as defined herein as a fragrance substance mixture and the use of a compound of formula (I) or a composition as defined herein for imparting, modifying and/or enhancing one or more olfactory notes selected from the group consisting of the notes ambergris, woody and animalic. Moreover, the present invention relates to fragrance substance compositions and perfumed products as defined herein, methods for producing a perfumed product, methods for perfuming a product and methods for perfuming hair, skin, textile fibres, surfaces and/or ambient air.

12 Claims, No Drawings

SECO-AMBRAKETALS

CROSS-REFERENCE TO RELATED APPLICATIONS

This application is a national stage application (under 35 U.S.C. § 371) of PCT/EP2020/076164, filed Sep. 18, 2020, which is incorporated herein by reference in its entirety.

The present invention primarily relates to compounds of formula (I) and compositions comprising one, two, three or more compound(s) of formula (I) or consisting of two, three or more compound(s) of formula (I). The invention further relates to methods for producing a compound of formula (I) or a composition as defined herein, the use of a compound of formula (I) as defined herein as a fragrance substance, the use of a composition as defined herein as a fragrance substance mixture and the use of a compound of formula (I) or a composition as defined herein for imparting, modifying and/or enhancing one or more olfactory notes selected from the group consisting of the notes ambergris, woody and animalic. Moreover, the present invention relates to fragrance substance compositions and perfumed products as defined herein, methods for producing a perfumed product, methods for perfuming a product and methods for perfuming hair, skin, textile fibres, surfaces and/or ambient air.

Further aspects and preferred embodiments of the present invention result from the following explanations, the attached examples and, in particular, the attached patent claims.

In the perfume industry, a large number of different compounds are known to be used to convey a pleasant odour. However, there is a constant need for new types of advantageous compounds which, in addition to their positive and original olfactory properties, have additional positive secondary properties.

In the search for suitable compounds, the skilled person is faced with the difficult task of either identifying suitable fragrances from a very large number of known compounds or producing new compounds with the desired properties. It is not possible to predict whether new compounds have an odour at all and whether this odour has desirable or undesirable olfactory properties. When a compound with a positive odour is found, it is also very questionable which odour it is and to what extent the compound also has positive secondary properties.

Many of the fragrances known so far have some significant disadvantages. For example, they often have a very limited stability and yield, low adhesion, low radiance, poor solubility and often have to be used in high dosages.

Very high demands are also placed on new fragrances. For example, they should have very good biodegradability and be dermatologically and toxicologically safe.

The note "ambergris" is one of the highly preferred olfactory notes in perfumes. It gives perfumes a special exclusivity and luxury. Originally ambergris was extracted from the digestive tract of sperm whales, nowadays ambergris fragrance substances from other sources are preferred. The disadvantage of many ambergris fragrance substances is that their olfactory impression is only gradually perceived, which is why it is particularly difficult to present the ambergris note in the top note of a perfume.

The best known ambergris fragrance substance ambroxide with the following structure

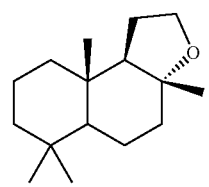 [SMILES: CC1(C)CCC[C@@]2(C)C1CC[C@@]1(C)OCC[C@@H]12]

is described to have a warm, slightly earthy, camphor-like, exotic-woody, animal-like note and is often used as a fixative due to its high tenacity. It is widely known by the brand name Ambroxan and is an auto-oxidation product of ambrein. Ambrein is a triterpene alcohol that is the chief constituent of ambergris as found in the digestive tract of sperm whales.

WO 2015/036402 A1 discloses compounds of the following formula

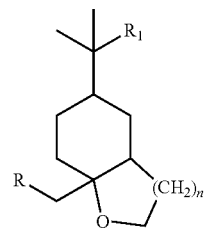

wherein R is H, methyl, ethyl, O-methyl or O-ethyl, $R_1$ is H, methyl, ethyl, O-methyl or O-ethyl and n is 1 or 2 and which have an ambergris and/or woody olfactory note.

WO 2016/083372 A1 relates to compounds of the following formula

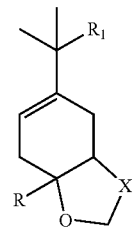

wherein R is methyl or ethyl, $R_1$ is H, methyl, ethyl, O-methyl or O-ethyl and X represents —$CH_2$— or —$CH_2$—$CH_2$— and which also have an ambergris and/or woody olfactory note.

WO 2018/233804 A1 relates primarily to the use of one or more compounds of the following formula

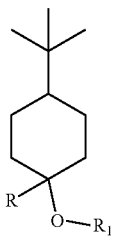

as perfume, wherein R represents methyl or ethyl and $R_1$ represents H, methyl or ethyl, particularly to impart, modify and/or enhance one or more olfactory notes selected from the group consisting of ambergris, indole and woody.

The object of the present invention was to provide compounds which do not have or mitigate the disadvantages of the prior art mentioned above. In particular, the object of the invention was to make available fragrance substances which are able to impart, modify and/or enhance the olfactory note ambergris and furthermore have positive secondary properties, such as good biodegradability and/or high dermatological compatibility.

The primary assigned object is solved according the invention by a compound of formula (I)

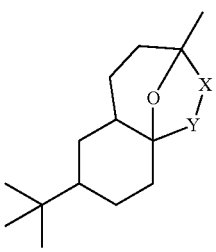

(I)

wherein X and Y are selected from the group consisting of —O— and —CH$_2$—, respectively, and the following applies: When X is —O—, then Y is —CH$_2$—, and when X is —CH$_2$—, then Y is —O—.

Hence, a compound of formula (I) is either a compound of formula (Ia) or of formula (Ib) as shown below:

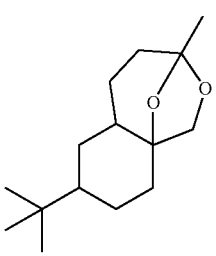

(Ia)

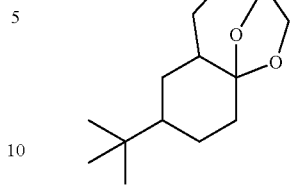

(Ib)

A compound of formula (I) or of formula (Ia) or of formula (Ib) according to the invention can be used in any stereoisomeric form. Within the scope of the present invention any mixture of stereoisomers of the compounds of formula (I) or of the compound of formula (Ia) or of the compound of formula (Ib) may be used, for example a mixture of diastereoisomers, a mixture of enantiomers or a racemate. Thus, the term "compounds of formula (I)" also includes, for the purposes of this text, the said mixtures of different stereoisomers of the compound(s) of formula (I). The term "compounds of formula (Ia)" includes, for the purposes of this text, the said mixtures of different stereoisomers of the compound of formula (Ia) and the term "compounds of formula (Ib)" includes, for the purposes of this text, the said mixtures of different stereoisomers of the compound of formula (Ib).

What is said herein for a compound of formula (I) or of formula (Ia) or of formula (Ib) applies accordingly to a mixture of stereoisomers of the compound(s) of formula (I) or of formula (Ia) or of formula (Ib) and to individual stereoisomers of the compound(s) of formula (I) or (Ia) or (Ib).

Moreover, what is said herein for a compound of formula (I) applies accordingly to compounds of formula (Ia) and to compounds of formula (Ib), which are compounds of formula (I).

Surprisingly, the compounds according to the present invention have an ambergris, woody and/or animalic odour.

In addition, they exhibit high stability and extensiveness, very good adhesion, very high radiance, a low odour threshold value, very good solubility and miscibility, low tendency to react with other fragrances, very good dermatological and toxicological compatibility and very good biodegradability.

A further advantage of the compounds according to the present invention is their high odour intensity at comparatively low dosage. This is of particular interest for reasons of environmental cleanliness, as the amount of substances released into the environment can be kept to a minimum. Furthermore, the ambery or ambergris note is perceived particularly quickly, so that the compounds are suitable for use as top notes in a perfume oil, for example.

The compounds of formula (I) are very stable and also show a high stability under unfavourable conditions, such as high oxygen content, high content of oxidants or reducing agents, high temperatures and under extreme pH conditions.

Particularly preferred compounds of formula (I) and their odour description are shown in Table 1 below:

TABLE 1

| Compound | Structure | Odour description |
|---|---|---|
| 1 | 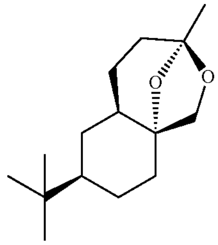 [SMILES: CC(C)(C)[C@@H]1CC[C@]23CO[C@](C)(CC[C@@H]2C1)O3] | Ambery, ambraketal-like, woody |
| 2 | 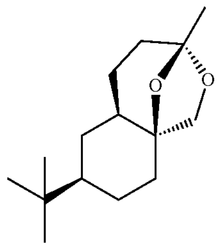 [SMILES: CC(C)(C)[C@@H]1CC[C@@]23CO[C@@](C)(CC[C@@H]2C1)O3] | Woody, cedar wood, animalic |
| 3 + 4 | | Woody, ambery, ambergris-like |

The compounds of formula (I) are characterised by the fact that they have a particularly complex, radiant and highly intensive ambery or ambergris note at low dosage. In addition, they have a woody odour, so that the particularly desired combination of ambery or ambergris and wood notes is created.

The present invention also relates to compositions comprising one, two, three or more compound(s) of formula (I) or consisting of two, three or more compound(s) of formula (I).

Preferably, the present invention relates to compositions comprising one, two, three or more compound(s) of formula (Ia) and/or one, two, three or more compound(s) of formula (Ib).

More preferably, the present invention relates to compositions consisting of two, three or more compound(s) of formula (Ia) or of two, three or more compound(s) of formula (Ib) or of one, two, three or more compound(s) of formula (Ia) and one, two, three or more compound(s) of formula (Ib).

Several synthetic routes towards the compounds of formula (I) are possible.

According to another aspect, the present invention thus relates to a method for producing a compound of formula (I) as defined herein or a composition as defined herein, comprising at least one, two, three or more of the reaction steps (i) to (v) as shown below.

The starting materials of step (i) of the method according to the invention, tert-butylcyclohexanone and tert-butyl acrylate, may be synthesised or are commercially available. They may be reacted, for example, with pyrrolidin, acetic acid and 4-methoxyphenol to the product of step (i) of the method according to the invention.

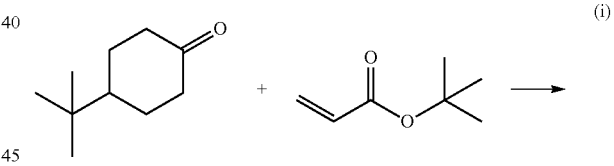

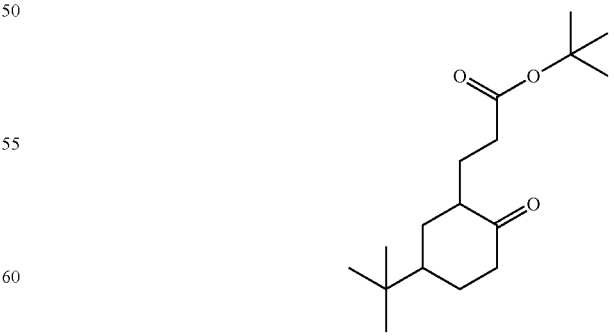

In step (ii), the ketone obtained in step (i) of the method according to the invention is reacted to an alkene, e.g. by subjecting it to a Wittig reaction with methyltriphenylphosphonium bromide (MePPh$_3$Br) in diethyl ether.

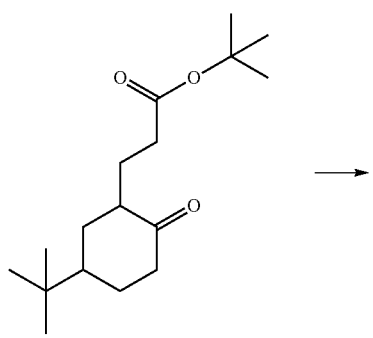

(ii)

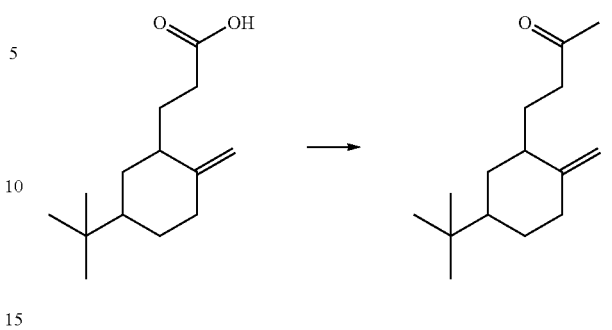

(iv)

Finally, in step (v) of the method according to the invention, the compound of formula (I) (or of formula (Ia)) is obtained by intramolecular cyclisation. This may be achieved, for example, by dihydroxylation of the double bond of the ketone obtained in step (iv) followed by in situ cyclisation to the compound of formula (I) (or of formula (Ia)) or by epoxidation of the double bond of the ketone obtained in step (iv) followed by in situ cyclisation to the compound of formula (I) (or of formula (Ia)).

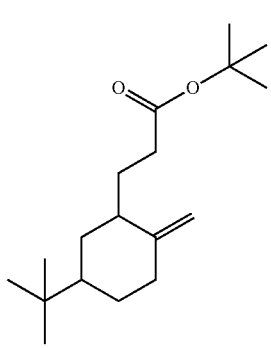

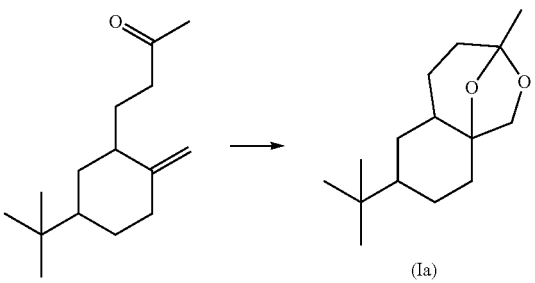

(v)

In step (iii) of the method according to the invention, the ester of the product of step (ii) is cleaved, e.g. with the base potassium hydroxide in methanol.

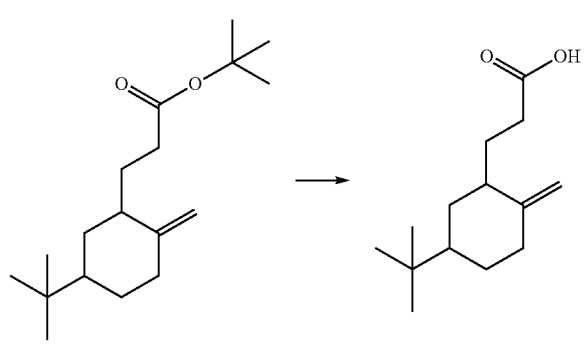

(iii)

Another aspect of the present invention relates to a method for producing a compound of formula (I) as defined herein or a composition as defined herein, comprising at least one, two, three or more of the reaction steps (i) to (vii) as shown below.

The starting materials of step (i) of the method according to the invention, tert-butylcyclohexanone and tert-butyl acrylate, may be synthesised or are commercially available. They may be reacted, for example, with pyrrolidin, acetic acid and 4-methoxyphenol to the product of step (i) of the method according to the invention.

In step (iv) of the method according to the invention, the carboxylic acid of the product of step (iii) is reduced to a ketone, e.g. with the aid of methyl lithium in tetrahydrofuran.

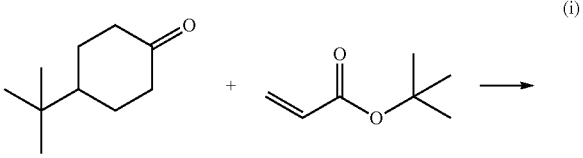

(i)

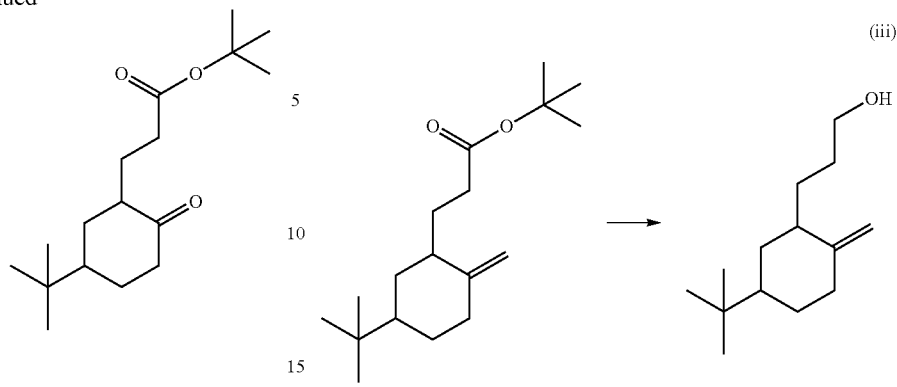

In step (ii), the ketone obtained in step (i) of the method according to the invention is reacted to an alkene, e.g. by subjecting it to a Wittig reaction with methyltriphenylphosphonium bromide (MePPh₃Br) in diethyl ether.

In step (iv) of the method according to the invention, the alcohol obtained in step (iii) is converted into an aldehyde, for example with Dess-Martin periodinane in dichloromethane.

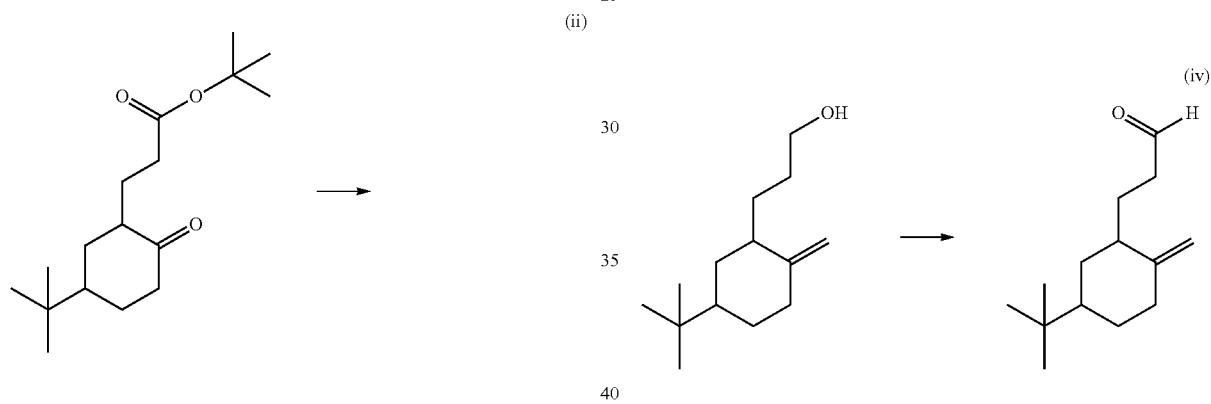

In step (iii) of the method according to the invention, the protected carboxylic acid of the product of step (ii) is reduced to an alcohol, for example with lithium aluminium hydride in tetrahydrofuran.

In step (v) of the method according to the invention, the aldehyde obtained in step (iv) is converted into an alcohol, for example with methyl lithium in tetrahydrofuran.

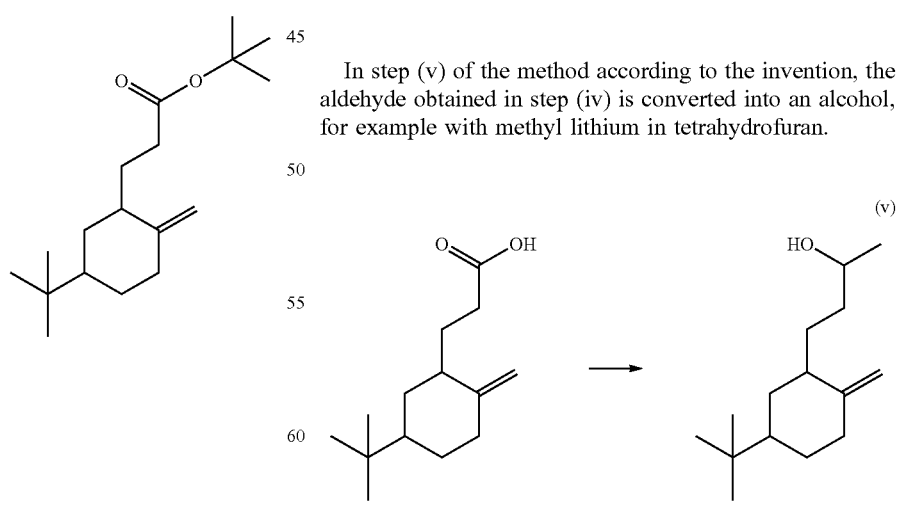

In step (vi) of the method according to the invention, the alcohol obtained in step (v) is converted into a ketone, for example with Dess-Martin periodinane in dichloromethane.

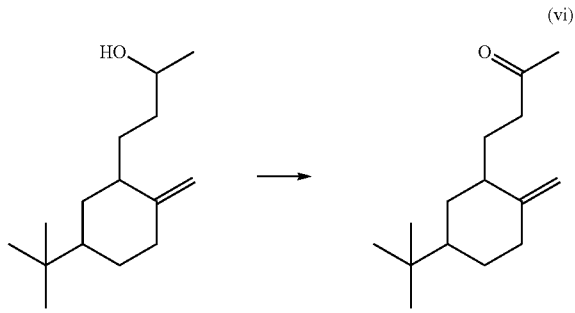 [SMILES: C=C1CCC(C(C)(C)C)CC1CCC(C)O ; C=C1CCC(C(C)(C)C)CC1CCC(C)=O]

(vi)

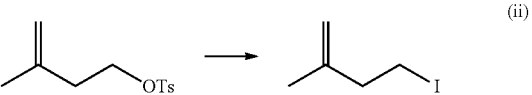

In step (iii) of the method according to the invention, the product of step (ii) is reacted with tert-butylhexanone.

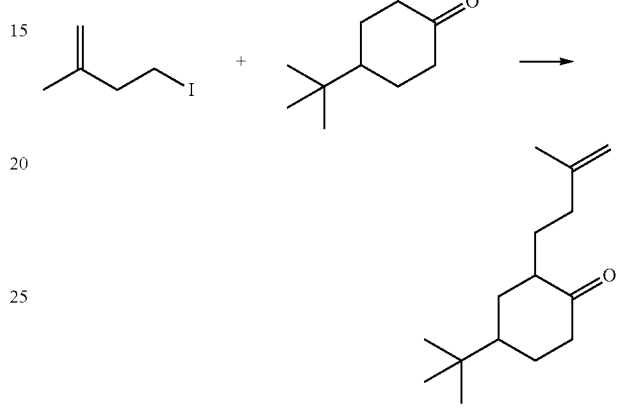

Finally, in step (vii) of the method according to the invention, the compound of formula (I) (or of formula (Ia)) is obtained by intramolecular cyclisation. This may be achieved, for example, by dihydroxylation of the double bond of the ketone obtained in step (vi) followed by in situ cyclisation to the compound of formula (I) (or of formula (Ia)) or by epoxidation of the double bond of the ketone obtained in step (vi) followed by in situ cyclisation to the compound of formula (I) (or of formula (Ia)).

Finally, in step (iv) of the method according to the invention, the compound of formula (I) (or of formula (Ib)) is obtained by intramolecular cyclisation. This may be achieved, for example, by dissolving the product of step (iii) in ethyl acetate and acetonitrile and dihydroxylating it with an aqueous solution of ruthenium(III) chloride hydrate and sodium periodate.

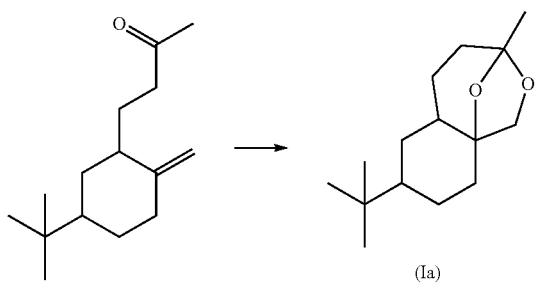

(vii)

(Ia)

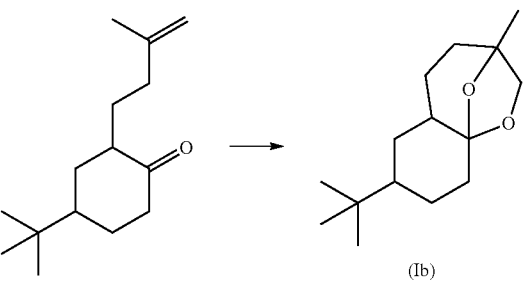

(iv)

(Ib)

Another aspect of the present invention relates to a method for producing a compound of formula (I) as defined herein or a composition as defined herein, comprising at least one, two, three or more of the reaction steps (i) to (iv) as shown below.

The starting material of step (i) of the method according to the invention, 3-methyl-3-buten-1-ol, may be synthesised or is commercially available.

In step (i) of the method according to the invention, the alcohol group is protected by a toluenesulfonyl (Ts) protecting group, for example by reaction with p-toluenesulfonyl chloride in pyridine.

Another aspect of the present invention relates to the use of a compound of formula (I) (or of formula (Ia) or of formula (Ib)) as defined herein as a fragrance substance.

A further aspect of the present invention relates to the use of a composition as defined herein as a fragrance substance mixture.

Preferably, the compound(s) of formula (I) or the compositions as defined herein are used for imparting, modifying and/or enhancing one or more olfactory notes selected from the group consisting of the notes ambergris, woody and animalic, preferably for imparting, modifying and/or enhancing the olfactory note ambergris.

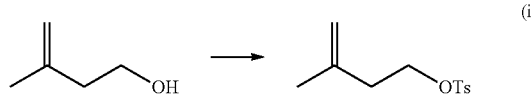

(i)

In step (ii) of the method according to the invention, the product of step (i) is converted into an iodide, for example by reaction with sodium iodide in acetone.

Another aspect of the present invention relates to fragrance substance compositions comprising or consisting of
(i) a compound of formula (I) as defined herein, or
(ii) a composition as defined herein,
and one or more additional fragrance substances.

Within the framework of the present text, additional fragrance substances are fragrance substances that are not compounds of formula (I).

Examples of additional fragrance substances that can be advantageously combined with the compounds of formula (I) (or of formula (Ia) or of formula (Ib)) as defined herein within the scope of the present invention can be found, for example, in S. Arctander, Perfume and Flavor Materials, Vol. I and II, Montclair, N. J. 1969, Eigenverlag, or K. Bauer et al., Common Fragrance and Flavor Materials, 4th Edition, Wiley-VCH, Weinheim 2001.

To be mentioned in detail: Extracts from natural raw materials such as essential oils, concretes, absolues, resins, resinoids, balsams, tinctures such as ambra tincture; amyris oil; angelica seed oil; angelica root oil; anise oil; valerian oil; basil oil; tree moss absolute; bay oil; mugwort oil; benzoe resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill herb oil; dill seed oil; eau de brouts absolute; oak moss absolute; elemi oil; tarragon oil; *Eucalyptus citriodora* oil; *eucalyptus* oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; chamomile oil blue; roman chamomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; *Litsea cubeba* oil; bay leaf oil; macis oil; marjoram oil; mandarin oil; massoi rind oil; mimosa absolute; musk seed oil; musk tincture; muscat sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petit grain oil; peppermint oil; pepper oil; pimento oil; pine oil; poley oil; rose absolute; rosewood oil; rose oil; rosemary oil; sage oil Dalmatian; sage oil Spanish; sandalwood oil; celery seed oil; spiked lavender oil; star anise oil; styrax oil; marigold oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine yeast oil; wormwood oil; wintergreen oil; ylang oil; ysop oil; zibet absolute; cinnamon leaf oil; cinnamon bark oil and fractions thereof, or ingredients isolated therefrom.

Moreover, the additional fragrance substances can be fragrance substances from the group
of hydrocarbons, such as e.g. 3-carene; α-pinene; β-pinene; α-terpinene; γ-terpinene; p-cymol; bisabolene; camphene; caryophyllene; cedrene; farnesene; limonene; longifolene; myrcene; ocimene; valencene; (E,Z)-1,3,5-undecatriene; styrene; diphenylmethane;
of aliphatic alcohols such as e.g. hexanol; octanol; 3-octanol; 2,6-dimethylheptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;
of aliphatic aldehydes and their acetals such as e.g. hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetal; 1,1-dimethoxy-2,2,5-trimethyl-4-hexene; citronellyl oxyacetaldehyde; 1-(1-methoxy-propoxy)-(E/Z)-3-hexene;
of aliphatic ketones and their oximes such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;
of aliphatic sulphur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;
of aliphatic nitriles such as e.g. 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;
of esters of aliphatic carboxylic acids, e.g. (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl crotonate;
of acyclic terpene alcohols such as e.g. geraniol; nerol; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerates, pentanoates, hexanoates, crotonates, tiglinates and 3-methyl-2-butenoates;
of acyclic terpene aldehydes and ketones such as e.g. citronellal; 7-methoxy-3,7-dimethyloctanal; 2,6,10-trimethyl-9-undecenal; geranylacetone; and the dimethyl and diethyl acetals of geranial, neral;
of cyclic terpene alcohols such as e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and their formates, acetates, propionates, isobutyrates, butyrates, isovalerianates, pentanoates, hexanoates, crotonates, tiglinates and 3-methyl-2-butenoates;
of cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethyl-ionone; alpha-iron; beta-damascenone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalen-8 (5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedrylketone); of cyclic alcohols such as e.g. 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols such as e.g. alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers such as e.g. cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyl-dodecahydro-naphtho[2,1-b]furane; 3a-ethyl-6,6,9a-trimethyldodecahydronaphtho[2,1b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic and macrocyclic ketones such as e.g. 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopenta-decanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of cycloaliphatic aldehydes such as e.g. 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

of cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-Tetramethyl-1,2,3,4,5,6,7,8-octahydro-2-naphtalenylmethylketone; methyl-2,6,10-trimethyl-2,5,9-cyclododecatrienylketone; tert.-butyl-(2,4-dimethyl-3-cyclohexen-1-yl)ketone;

of esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclo-pentylcyclopentylcrotonate; 3-pentyltetrahydro-2H-pyran-4-yl acetate; decahydro-2,5,5,8a-tetramethyl-2-naphthyl acetate; 4,7-methano-3a,4,5,6,7,7a-hexa-hydro-5, or 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

of esters of cycloaliphatic alcohols such as e.g. 1-cyclohexylethylcrotonate;

of esters of cycloaliphatic carboxylic acids such as e.g. allyl-3-cyclohexylpropionate; allylcyclohexyloxyacetate; cis- and trans-methyldihydrojasmonate; cis- and trans-methyljasmonate; methyl-2-hexyl-3-oxocyclopentanecarboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

of araliphatic alcohols such as e.g. benzyl alcohol; 1-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids such as e.g. benzylacetate; benzyl propionate; benzyl isobutyrate; benzyl isovalerianate; 2-phenylethyl acetate; 2-phenylethyl propionate; 2-phenylethyl isobutyrate; 2-phenyl ethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

of araliphatic ethers such as e.g. 2-phenylethyl methyl ether; 2-phenylethyl isoamyl ether; 2-phenylethyl-1-ethoxyethyl ether; phenylacetaldehyde dimethylacetal; phenylacetaldehyde diethylacetal; hydratropaaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-isobutylphenyl)propanal; 3-(4-tert.-butyl-phenyl)propanal; cinnamic aldehyde; alpha-butyl cinnamic aldehyde; alpha-hexyl cinnamic aldehyde; 3-methyl-5-phenylpentanal; 4-methoxybenzaldehyde; 4-hydroxy-3-methoxybenzaldehyde; 4-Hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones such as e.g. acetophenone; 4-methylacetophenone; 4-methoxyacetophenone; 4-tert.-butyl-2,6-dimethylaceto-phenone; 4-phenyl-2-butanone; 4-(4-hydroxyphenyl)-2-butanone; 1-(2-naphtha-lenyl)ethanone; 2-benzofuranylethanone; (3-methyl-2-benzofuranyl)ethanone; benzophenone; 1,1,2,3,3,6-hexamethyl-5-indanylmethylketone; 6-tert-butyl-1,1-di-methyl-4-indanylmethylketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-aceto-naphthone;

of aromatic and araliphatic carboxylic acids and their esters such as e.g. benzoic acid; phenylacetic acid; methyl benzoate; ethyl benzoate; hexyl benzoate; benzyl benzoate; methyl phenyl acetate; ethyl phenyl acetate; geranyl phenyl acetate; phenylethyl phenyl acetate; methyl cinnamate; ethyl cinnamate; benzyl cinnamate; phenylethyl cinnamate; cinnamyl cinnamate; allyl phenoxy acetate; methyl salicylate; hexyl salicylate; cyclohexyl salicylate; cis-3-hexenyl salicylate; benzylsalicylate; phenylethyl salicylate; methyl 2,4-dihydroxy-3,6-dimethylbenzoate; ethyl-3-phenylglycidate; ethyl-3-methyl-3-phenylglycidate;

of nitrogen-containing aromatic compounds such as e.g. 2,4,6-trinitro-1,3-dimethyl-5-tert.butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methylanthranilate; methy-N-methylanthranilate; Schiff bases of methylanthranilate with 7-hydroxy-3,7-dimethyloctanal, 2-methyl-3-(4-tert.-butyl-phenyl)propanal or 2,4-dimethyl-3-cyclohexene carbaldehyde; 6-isopropyl quinoline; 6-isobutylquinoline; 6-sec.-butylquinoline; 2-(3-phenylpropyl)pyridine; indole; skatol; 2-methoxy-3-isopropylpyrazine; 2-isobutyl-3-methoxypyrazine;

of phenols, phenyl ethers and phenylesters such as estragol; anethol; eugenyl methylether; isoeugenol; isoeugenyl methylether; thymol; carvacrol; diphenylether; beta-naphthylmethylether; beta-naphthylethylether; beta-naphthyliso-butylether; 1,4-dimethoxybenzol; eugenylacetate; 2-methoxy-4-methylphenol; 2-ethoxy-5-(1-propenyl)phenol; p-kresylphenylacetate;

of heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones such as e.g. 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadeca-nolide; 9-hexadecene-1,16-olide; 10-oxa-1,16-hexadecanolide; 11-oxa-1,16-hexa-decanolide; 12-oxa-1,16-hexadecanolide; ethylene-1,12-dodecanedioate; ethylene-1,13-tridecanedioate; 2,3-dihydrocoumarin; octahydrocoumarin.

According to a preferred embodiment of the fragrance substance composition according to the invention, one or more compound(s) of formula (I) (or of formula (Ia) and/or (Ib)) according to the invention is/are combined with one or more, particularly preferably with two, three, four, five or more, additional fragrance substances.

Fragrance substance compositions according to the invention, which contain one or more compound(s) of formula (I) (or of formula (Ia) and/or (Ib)), can be in liquid form, undiluted or diluted with solvents. Preferred solvents are ethanol, isopropanol, diethylene glycol monoethyl ether, glycerol, propylene glycol, 1,2-butylene glycol, dipropylene glycol, diethyl phthalate, triethyl citrate, isopropyl myristate, triacetine and diacetine.

In addition, fragrance substance compositions according to the invention may be adsorbed to a carrier which ensures both a fine distribution of the fragrance substances in the product and a controlled release during application. Such carriers may be porous inorganic materials such as light sulphate, silica gels, zeolites, gypsums, clays, clay granules, gas concrete, etc. or organic materials such as wood, cellulose-based materials, sugars, dextrins (e.g. maltodextrin) or plastics such as PVC, polyvinyl acetates or polyurethanes. The combination of fragrance substance composition according to the invention and carrier is also to be understood as fragrance substance composition according to the invention or may be present as a product according to the invention (as described below).

Fragrance substance compositions or products (as described herein below) according to the invention may also be present in microencapsulated form, spray-dried form, as inclusion complexes or as extrusion products and—in case of a fragrance substance composition—may be added in this form to a product to be perfumed (as described herein below).

If applicable, the properties of such modified compositions or products can be further optimised by so-called "coating" with suitable materials in view of a more targeted release of fragrance, preferably using wax-like plastics such as e.g. polyvinyl alcohol. The resulting products in turn are products according to the invention.

Microencapsulation can, for example, be achieved by the so-called coacervation process with the aid of capsule materials, e.g. polyurethane-like substances or soft gelatine.

Spray-dried products are preferably produced by spray-drying an emulsion or dispersion containing the fragrance substance composition, whereby modified starches, proteins, dextrins and vegetable gums can be used as carriers.

Inclusion complexes can be prepared e.g. by incorporating dispersions of the fragrance substance composition and cyclodextrins or urea derivatives into a suitable solvent, e.g. water.

Extrusion products can be obtained e.g. by fusing the fragrance substance compositions with a suitable wax-like substance and by extrusion followed by solidification, if applicable in a suitable solvent, e.g. isopropanol.

Another aspect of the present invention relates to perfumed products comprising a compound of formula (I) as defined herein or a composition as defined herein or a fragrance substance composition as defined herein.

Preferably, the perfumed product according to the invention is selected from the group consisting of detergents and cleaning agents, hygiene or care products, preferably in the field of body and hair care, cosmetics and household, preferably from the group consisting of perfume extracts, eau de parfums, eau de toilettes, aftershave lotions, eau de colognes, pre-shave products, splash colognes, perfumed refreshing wipes, acidic, alkaline or neutral detergents, textile fresheners, ironing aids, liquid detergents, powder detergents, laundry pre-treatments, fabric softeners, washing soaps, washing tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants, antiperspirants, decorative cosmetic products, candles, lamp oils, incense sticks, insecticides, repellents and fuels.

Preferably, in the perfumed products according to the invention, the one or more compound(s) of formula (I) is/are contained in a sensorially effective amount, preferably in an amount sufficient for a consumer to detect one or more olfactory notes selected from the group consisting of the notes ambergris, woody and animalic, preferably for a consumer to detect the olfactory note ambergris.

More preferably, in a perfumed product according to the invention as defined herein, the total amount of one or more compound(s) of formula (I), based on the total weight of the product, is in the range from 0.00001 to 10% by weight, preferably from 0.0001 to 5% by weight, more preferably from 0.001 to 2% by weight, more preferably from 0.005 to 1% by weight.

Another aspect of the present invention relates to a method for producing a perfumed product, preferably a perfumed product as defined herein, comprising or consisting of the following steps:
(i) providing a compound of formula (I) as defined herein or a composition as defined herein or a fragrance substance composition as defined herein,
(ii) providing one or more further components of the perfumed product to be produced, and
(iii) contacting or mixing the further components provided in step (ii) with a sensorially effective amount of the components provided in step (i).

Another aspect of the present invention relates to a method for perfuming a product, comprising or consisting of the following steps:
(a) providing
  (i) a compound of formula (I) as defined herein, or
  (ii) a composition as defined herein, or
  (iii) a fragrance substance composition as defined herein,
and
(b) adding the (i) compound of formula (I) as defined herein or the (ii) composition as defined herein or the (iii) fragrance substance composition as defined herein to the product to be perfumed in a sensorially effective amount, preferably in an amount sufficient to impart, enhance and/or modify one or more olfactory notes selected from the group consisting of the notes ambergris, woody and animalic, preferably the olfactory note ambergris.

Hence, the (i) compound of formula (I) as defined herein or the (ii) composition as defined herein or the (iii) fragrance substance composition as defined herein is added in step (b) of said method for perfuming a product in an amount sufficient for the consumer of the product to detect one or more olfactory notes selected from the group consisting of the notes ambergris, woody and animalic, preferably for a consumer to detect the olfactory note ambergris.

Another aspect of the present invention relates to a method for perfuming hair, skin, textile fibres, surfaces and/or ambient air comprising or consisting of the following steps:
(a) providing
  (i) a compound of formula (I) as defined herein and preferably also a surfactant or a surfactant mixture, or
  (ii) a composition as defined herein, preferably containing a surfactant or a surfactant mixture, or
  (iii) a fragrance substance composition as defined herein, preferably containing a surfactant or a surfactant mixture, or
  (iv) a perfumed product as defined herein, preferably containing a surfactant or a surfactant mixture,
and
(b) applying or introducing the (i) compound and preferably also a surfactant or a surfactant mixture, or the (ii) composition, or the (iii) fragrance substance composition, or the (iv) perfumed product of step (a) to the hair or skin or fibres or surface to be perfumed, or into the ambient air to be perfumed, in a sensorially effective amount, preferably in an amount sufficient for the consumer to detect one or more olfactory notes selected from the group consisting of the notes ambergris, woody and animalic, preferably for a consumer to detect the olfactory note ambergris.

For preferred embodiments of the compounds of formula (I) (or of formula (Ia) or (Ib)) described herein, what has been stated in connection with the (fragrance substance) compositions, perfumed products, methods and uses according to the invention applies accordingly and vice versa.

In the following, the invention is explained in more detail using examples.

EXAMPLES

1. Synthesis Route I Towards Compounds of Formula (Ia)

1.1 Synthesis of tert-butyl 3-((1'R,5'R)-5'-(tert-butyl)-2'-oxocyclohexyl)propan-oate

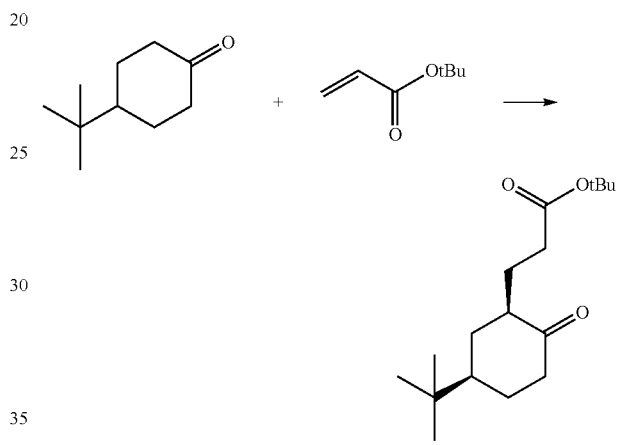

Tert-butylcyclohexanone (3.13 g, 20.07 mmol, 1.33 equiv.) was heated to 50° C. Pyrrolidine (0.25 mL, 3.01 mmol, 0.2 equiv.), $CH_3COOH$ (17 µL, 0.30 mmol, 0.03 equiv.) and 4-methoxyphenol (20 mg, 0.20 mmol, 0.02 equiv.) were added. The solution was heated to 70° C. and tert-butyl acrylate (1.5 mL, 10.04 mmol, 0.67 equiv.) was added dropwise. It was stirred for 24 h at 125° C. Since the tert-butyl acrylate had reacted off (GC control), additional tert-butyl acrylate (0.75 mL, 5.02 mmol, 0.33 equiv.) was added dropwise. The reaction mixture was stirred for another 16 h and then cooled down to room temperature. 10% $NH_4Cl$ solution (20 mL) was added and the phases were separated. The aqueous phase was extracted with methyl-tert-butylether (MTBE, 2×30 mL) and the combined organic phases were washed with water (50 mL). The extracts were dried with $Na_2SO_4$, filtered and the volatile components removed under reduced pressure. The raw product was purified by Kugelrohr distillation (T=110° C., p=0.64 mbar to T=170° C., p=0.59 mbar) and the product was obtained as a colourless liquid (2.67 g, 9.44 mmol, 63% as 4:1 isomer mixture (cis/trans)).

TLC: $R_f$=0.24 (ethyl acetate/cyclohexane, 5:95)

Boiling point (bp): $T_b$=120° C.-122° C. (p=98 mbar)

$^1$H-NMR (400 MHz, $CDCl_3$) δ=2.43-2.20 (m, 5H, C(=O)$CH_2$, $(CH_3)_3$COC(=O)$CH_2$, C(=O)CH), 2.16-2.06 (m, 2H, 2×$C_q$CHC(H)H'), 2.06-1.98 (m, 1H, CHC(H)H'$CH_2$), 1.62-1.54 (m, 1H, $C_q$CH), 1.46-1.42 (m, 2H, $C_q$CHC(H)H', CHC(H)H'$CH_2$), 1.44 (s, 9H, C(=O)OC$(CH_3)_3$), 1.16 (q, J=12.7 Hz, 1H, $C_q$CHC(H)H'), 0.91 (s, 9H, C$(CH_3)_3$)

$^{13}$C-NMR (101 MHz, CDCl$_3$) δ=212.94 (C=O), 173.07 (C(=O)OR), 80.08 (C$_q$(CH$_3$)$_3$O), 48.86 (C(=O)CH), 47.15 (C$_q$CH), 41.71 (C(=O)CH$_2$), 35.22 (C$_q$CHCH$_2$), 33.12 (ROC(=O)CH$_2$), 32.46 (C(CH$_3$)$_3$), 28.79 (C$_q$CHCH$_2$), 28.14 (OC(CH$_3$)$_3$), 27.66 (C(CH$_3$)$_3$), 24.89 (CHCH$_2$CH$_2$)

IR (GC/FT-IR): ṽ=2969 (s), 2878 (w), 1732 (s), 1372 (m), 1250 (w), 1158 (s) cm$^{-1}$

HRMS (ESI-TOF): Calculated for C17H30O3 [M+Na]$^+$ 305.2093; found 305.2087

1.2 Synthesis of tert-butyl 3-((1'R,5'R)-5'-(tert-butyl)-2'-methylenecyclohexyl)propanoate

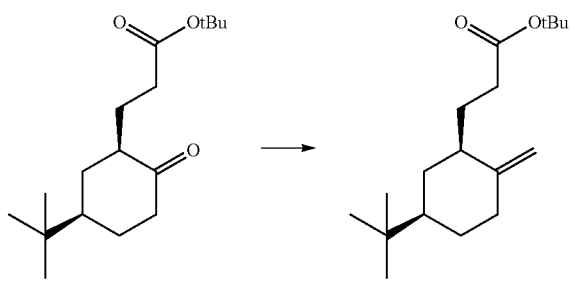 [SMILES: CC(C)(C)OC(=O)CC[C@@H]1C[C@H](C(C)(C)C)CCC1=O ; C=C1CC[C@@H](C(C)(C)C)C[C@H]1CCC(=O)OC(C)(C)C]

For a Wittig reaction, MePPh$_3$Br (39.4 g, 110 mmol, 1.3 equiv.) was dissolved in 200 mL Et$_2$. KOtBu (14.3 g, 127 mmol, 1.5 equiv.) was added and the suspension stirred for 1 h under reflux at 38° C. The mixture was then cooled down and the product of the reaction described in item 1.1 above (25.0 g, 84.9 mmol) in 250 mL Et$_2$O was added dropwise. After the addition was stopped, it was again heated to 38° C. and stirred at this temperature for 6 hours. The reaction was cooled to room temperature and H$_2$O (150 mL) and pentane (150 mL) were added. After filtration and separation of the phases, the aqueous phase was extracted with Et$_2$O (3×100 mL). The combined organic phases were washed with H$_2$O (300 mL) and dried with Na$_2$SO$_4$. After filtration, the volatile components were removed under reduced pressure. The accumulated solids were filtered off and washed with pentane (300 mL). The volatile components of the filtrate were removed under reduced pressure. The raw product was purified by Kugelrohr distillation (T=90° C., p=0.69 mbar to T=137° C., p=0.67 mbar) and the product was obtained as a colourless liquid (20.2 g, 71.5 mmol, 81%, 96:4 isomer mixture (cis/trans)).

TLC: R$_f$=0.27 (ethyl acetate/cyclohexane, 2.5:97.5)

$^1$H-NMR (400 MHz, CDCl$_3$) δ=4.69 (d, J=1.1 Hz, 1H, C=C(H)H'), 4.57 (d, J=1.1 Hz, 1H, C=C(H)H'), 2.36 (dt, J=12.8, 3.7 Hz, 1H, C(=CH$_2$)C(H)H'), 2.33-2.27 (m, 2H, ROC(=O)CH$_2$), 2.02-1.82 (m, 5H, C(=CH$_2$)C(H)H', 2×C$_q$CHC(H)H', C(=CH$_2$)CH, CHC(H)H'CH$_2$), 1.64-1.54 (m, 1H, CHC(H)H'CH$_2$), 1.45 (s, 9H, C(=O)OC(CH$_3$)$_3$), 1.23 (tt, J=12.2, 3.1 Hz, 1H, C$_q$CH), 1.12-0.98 (m, 1H, C$_q$CHC(H)H'), 0.85 (s, 9H, C(CH$_3$)$_3$), 0.73 (q, J=11.6 Hz, 1H, C$_q$CHC(H)H')

$^{13}$C-NMR (101 MHz, CDCl$_3$) δ=173.44 (C(=O)OR), 152.60 (C=CH$_2$), 103.97 (C=CH$_2$), 79.98 (C$_q$(CH$_3$)$_3$O), 48.13 (C$_q$CH), 42.01 (C(=O)CH), 37.03 (C(=O)CH$_2$), 35.33 (C$_q$CHCH$_2$), 33.51 (ROC(=O)CH$_2$), 32.45 (C(CH$_3$)$_3$), 29.62 (C$_q$CHCH$_2$), 28.15 (OC(CH$_3$)$_3$), 27.77 (CHCH$_2$CH$_2$), 27.65 (C(CH$_3$)$_3$)

IR (GC/FT-IR): ṽ=3089 (w), 2950 (s), 2875 (m), 1744 (s), 1371 (m), 1250 (m), 1153 (s) cm$^{-1}$

HRMS (ESI-TOF): Calculated for C$_{18}$H$_{32}$O$_2$ [M+H]$^+$ 281.2481; found 281.2473

1.3 Synthesis of 3-((1'R,5'R)-5'-(tert-butyl)-2'-methylencyclohexyl)-propanoic acid

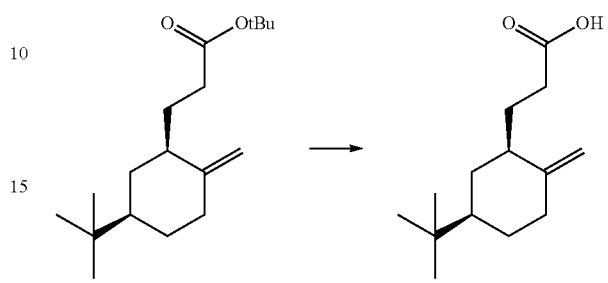

The product of the reaction described in item 1.2 above (4.02 g, 14.2 mmol) was dissolved in KOH (5% in MeOH, 20 mL) and stirred at room temperature for 2 days. 10% NH$_4$Cl solution (60 mL) was added and the product extracted with Et$_2$O (3×40 mL). The combined organic phases were washed with water (100 mL), dried with Na$_2$SO$_4$, filtered, and the volatile components were removed under reduced pressure. The product was obtained as a colourless liquid (3.15 g, 14.0 mmol, 99% as 96:4 isomer mixture (cis/trans)) and carried into the next step without further purification.

TLC: R$_f$=0.36 (ethyl acetate/cyclohexane, 10:90)

$^1$H-NMR (600 MHz, CDCl$_3$) δ=4.71 (d, J=1.5 Hz, 1H, C=C(H)H'), 4.56 (d, J=1.4 Hz, 1H, C=C(H)H'), 2.47-2.44 (m, 1H, C(H)H'COOH), 2.36 (ddd, J=13.0, 4.0, 2.8 Hz, 1H, CH$_2$=CC(H)H'), 2.05-1.94 (m, 2H, CH$_2$=CC(H)H', CHC(H)H'CH$_2$), 1.92-1.85 (m, 3H, 2×C$_q$CHC(H)H', CH$_2$=CCH), 1.67-1.59 (m, 1H, CHC(H)H'CH$_2$), 1.25 (tt, J=12.1, 3.2 Hz, 1H, C$_q$CH), 1.06 (qd, J=12.5, 4.1 Hz, 1H, C$_q$CHC(H)H'), 0.85 (s, 9H, C$_q$(CH$_3$)$_3$), 0.76 (q, J=12.7 Hz, 1H, C$_q$CHC(H)H')

$^{13}$C-NMR (151 MHz, CDCl$_3$) δ=179.77 (COOH), 152.33 (C=CH$_2$), 104.07 (C=CH$_2$), 48.05 (C$_q$CH), 41.94 (CH$_2$=CCH), 37.00 (CH$_2$=CCH$_2$), 35.48 (C$_q$CHCH$_2$), 32.46 (C(CH$_3$)$_3$), 31.96 (CH$_2$COOH), 29.63 (C$_q$CHCH$_2$), 27.64 (C(CH$_3$)$_3$), 27.48 (CHCH$_2$CH$_2$)

IR (GC/FT-IR): ṽ=3575 (m), 3089 (w), 2953 (s), 2874 (m), 1777 (s), 1371 (m), 1123 (s), 894 (w) cm$^{-1}$

MS (EI): m/z=224 [M]$^+$, 167 [M−(CH$_3$)$_3$C]$^+$, 57 [(CH$_3$)$_3$C]$^+$

HRMS (ESI-TOF): Calculated for C$_{14}$H$_{24}$O$_2$ [M+H]$^+$ 225.1855; found 225.1849

1.4 Synthesis of 4-((1'S,5'S)-5'-(tert-butyl)-2'-methylencyclohexyl)butan-2-one

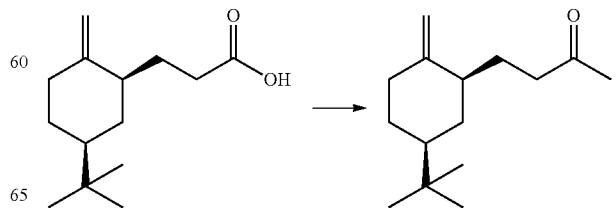

The product of the reaction described in item 1.3 above (7.00 g, 28.5 mmol) was dissolved in 60 mL THF and cooled to −78° C. MeLi (39.1 mL of a 1.6 M solution in Et$_2$O, 62.6 mmol, 2.2 equiv.) was added dropwise and the solution was stirred for 5 h at −78° C. The solution was then heated to room temperature and water (40 mL) was added. The phases were separated and the aqueous phase was extracted with Et$_2$O (3×50 mL). The organic phases were combined and washed with 5% NaCl solution (100 mL). The extracts were dried with Na$_2$SO$_4$, filtered and the volatile components removed under reduced pressure. The raw product was purified by column chromatography (250 mL SiO$_2$, 4-5% EtOAc in cyclohexane). The product was obtained as a colourless liquid (4.53 g, 20.4 mmol, 72%, 96:4 isomer mixture (cis/trans)).

TLC: $R_f$=0.40 (ethyl acetate/cyclohexane, 5:95)

$^1$H-NMR (400 MHz, CDCl$_3$) δ=4.69 (q, J=1.5 Hz, 1H, C(H)H'), 4.54 (q, J=1.4 Hz, 1H, C(H)H'), 2.52 (t, J=7.6 Hz, 2H, O=CCH$_2$), 2.36 (ddd, J=12.8, 3.9, 2.6 Hz, 1H, CH$_2$=CC(H)H'), 2.15 (s, 3H, O=CCH$_3$), 2.02-1.78 (m, 5H, CH$_2$=CC(H)H', 2×C$_q$CHC(H)H', CH$_2$=CCH, CHC(H)H'), 1.64-1.50 (m, 1H, CHC(H)H'), 1.24 (tt, J=12.1, 3.1 Hz, 1H, C$_q$CH), 1.05 (qd, J=12.6, 4.0 Hz, 1H, C$_q$CHC(H)H'), 0.85 (s, 9H, 3×CH$_3$), 0.75 (q, J=11.7 Hz, 1H, C$_q$CHC(H)H')

$^{13}$C-NMR (101 MHz, CDCl$_3$) δ=209.27 (C=O), 152.63 (C=CH$_2$), 103.98 (C=CH$_2$), 48.11 (C$_q$CH), 42.09 (CH$_2$=CCH), 41.75 (O=CCH$_2$), 37.03 (CH$_2$=CCH$_2$), 35.73 (C$_q$CHCH$_2$), 32.45 (C$_q$), 29.98 (O=CCH$_3$), 29.66 (C$_q$CHCH$_2$), 27.64 (C$_q$(CH$_3$)$_3$), 26.41 (CH$_2$=CCHCH$_2$)

IR (GC/FT-IR): ṽ=3089 (w), 2952 (s), 2874 (w), 1732 (m), 1368 (m), 893 (w) cm$^{-1}$

MS (EI): m/z=222 [M]$^+$, 165 [M−(CH$_3$)$_3$C]$^+$, 57 [(CH$_3$)$_3$C]$^+$

HRMS (ESI-TOF): Calculated for C$_{15}$H$_{26}$O [M+H]$^+$ 223.2062; found 223.2058

1.5 Synthesis of 4-((3'R,4'R,6'R)-6'-(tert-butyl)-1-oxaspiro[2.5]octan-4'-yl)butan-2-one (epoxide (a)) and 4-((3'S,4'R,6'R)-6'-(tert-butyl)-1-oxaspiro[2.5]octan-4'-yl)butan-2-one (epoxide (b))

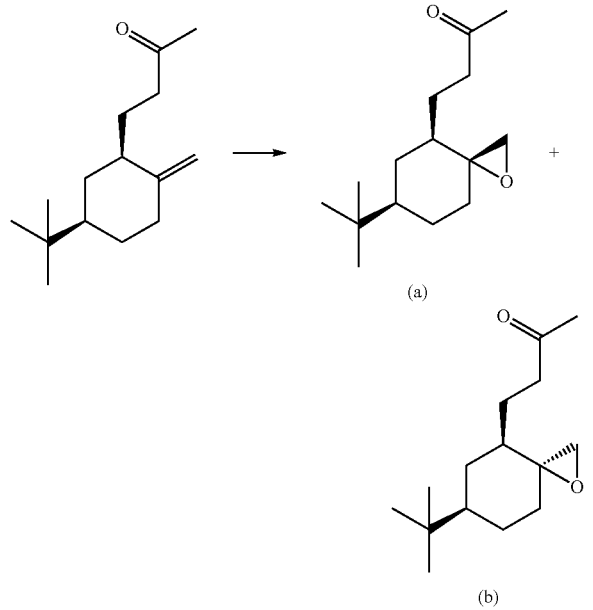

The product of the reaction described in item 1.4 above (1.90 g, 8.46 mmol) was dissolved in 20 mL CH$_2$Cl$_2$ and cooled to 0° C. At this temperature mCPBA (meta-chloroperbenzoic acid, 2.63 g, 15.2 mmol, 1.8 equiv.) was added and the reaction mixture was stirred at room temperature for 4 h. Water (10 mL) was added and the phases were separated. Subsequently, it was extracted with EtOAc (2×10 mL) and the combined organic phases were washed with 5% Na$_2$CO$_3$ solution (10 mL) and saturated NaCl solution (2×10 mL). The extracts were dried with Na$_2$SO$_4$, filtered and the volatile components were removed under reduced pressure. The raw product was purified by column chromatography (300 mL SiO$_2$, 10% EtOAc in cyclohexane). In the process the epoxides (a) (559 mg, 2.34 mmol, 26%) and (b) (1.19 g, 5.01 mmol, 59%) were isolated each as colourless liquids. The ratio of the two isomers was 3:7.

Epoxide (a):

TLC: $R_f$=0.19 (ethyl acetate/cyclohexane, 10:90)

$^1$H-NMR (400 MHz, CDCl$_3$) δ=2.76 (dd, J=4.5, 1.9 Hz, 1H, CC(H)H'O), 2.54-2.36 (m, 2H, CC(H)H'O, CH$_2$C=O), 2.13 (s, 3H, (C=O)CH$_3$), 1.98-1.81 (m, 3H, C(O)C(H)H', 2×C$_q$CHC(H)H'), 1.67 (ddt, J=12.1, 8.3, 4.2 Hz, 1H, C(O)CH), 1.59-1.51 (m, 1H, CHC(H)H'CH$_2$), 1.37-1.29 (m, 1H, C(O)C(H)H'), 1.23-1.06 (m, 3H, C$_q$CH, C$_q$CHC(H)H', CHC(H)H'CH$_2$), 0.88 (s, 9H, C(CH$_3$)$_3$), 0.91-0.82 (m, 1H, C$_q$CHC(H)H')

$^{13}$C-NMR (101 MHz, CDCl$_3$) δ=209.06 (C=O), 62.07 (C(O)CH$_2$), 49.59 (CCH$_2$O), 47.52 (C$_q$CH), 42.16 (CH$_2$C=O), 39.95 (C(O)CH), 35.50 (C(O)CH$_2$), 33.35 (C$_q$CHCH$_2$), 32.42 (C(CH$_3$)$_3$), 29.90 ((C=O)CH$_3$), 27.66 (C(CH$_3$)$_3$), 26.67 (C$_q$CHCH$_2$), 23.50 (CHCH$_2$CH$_2$)

MS (EI): m/z=238 [M]$^+$, 181 [M−(CH$_3$)$_3$C]$^+$, 57 [(CH$_3$)$_3$C]$^+$, 43 [CH$_3$C(=O)]$^+$

HRMS (ESI-TOF): Calculated for C$_{15}$H$_{26}$O$_2$ [M+H]$^+$ 239.2011; found 239.2000

Epoxide (b):

TLC: $R_f$=0.16 (ethyl acetate/cyclohexane, 10:90)

$^1$H-NMR (400 MHz, CDCl$_3$) δ=2.94 (d, J=4.2 Hz, 1H, CC(H)H'O), 2.54-2.43 (m, 1H, C(H)H'C=O), 2.49 (d, J=4.2 Hz, 1H, CC(H)H'O), 2.36 (ddd, J=17.0, 9.0, 6.4 Hz, 1H, C(H)H'C=O), 2.13 (s, 3H, (C=O)CH$_3$), 1.89-1.82 (m, 1H, C(O)C(H)H'), 1.81-1.69 (m, 3H, C(O)CH, 2×C$_q$CHC(H)H'), 1.52 (dddd, J=13.8, 9.0, 6.4, 4.5 Hz, 1H, CHC(H)H'CH$_2$), 1.40-1.22 (m, 3H, C(O)C(H)H', C$_q$CHC(H)H', CHC(H)H'CH$_2$), 1.15 (tt, J=11.7, 2.9 Hz, 1H, C$_q$CH), 1.04 (ddd, J=13.1, 10.6 Hz, 1H, C$_q$CHC(H)H'), 0.88 (s, 9H, C(CH$_3$)$_3$)

$^{13}$C-NMR (101 MHz, CDCl$_3$) δ=208.91 (C=O), 60.29 (C(O)CH$_2$), 51.08 (CCH$_2$O), 47.79 (C$_q$CH), 41.20 (CH$_2$C=O), 38.12 (C(O)CH), 35.17 (C(O)CH$_2$), 32.59 (C(CH$_3$)$_3$), 30.72 (C$_q$CHCH$_2$), 29.97 ((C=O)CH$_3$), 27.60 (C(CH$_3$)$_3$), 24.75 (C$_q$CHCH$_2$), 22.72 (CHCH$_2$CH$_2$)

IR (GC/FT-IR): ṽ=3046 (w), 2957 (s), 2878 (w), 1732 (m), 1368 (w) cm$^{-1}$

MS (EI): m/z=238 [M]$^+$, 181 [M−(CH$_3$)$_3$C]$^+$, 57 [(CH$_3$)$_3$C]$^+$, 43 [CH$_3$C(=O)]$^+$

HRMS (ESI-TOF): Calculated for C$_{15}$H$_{26}$O$_2$ [M+H]$^+$ 239.2011; found 239.2002

1.6 Synthesis of Compounds 1 and 2

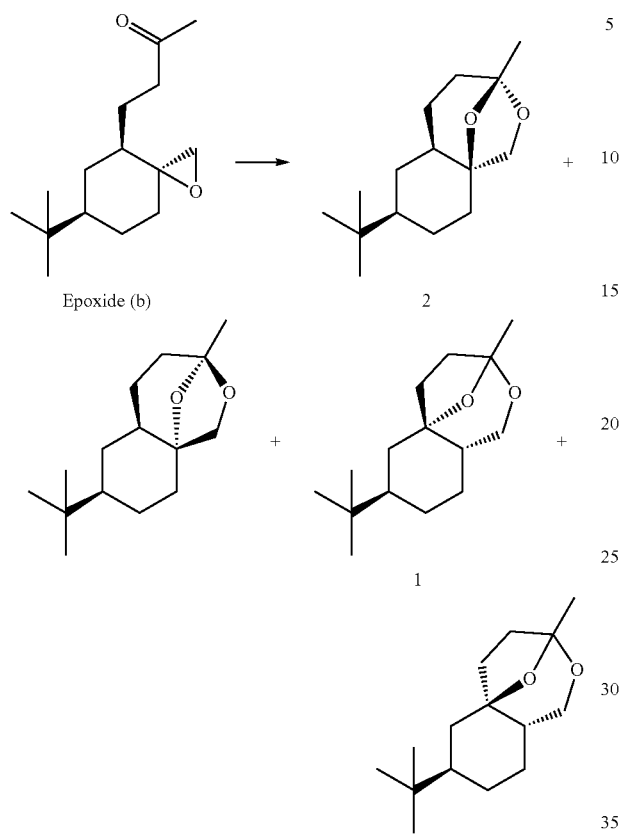

Epoxide (b) as obtained in item 1.5 above (152 mg, 608 μmol) was dissolved in 8 mL CH$_2$Cl$_2$ and BF$_3$ (8 mg, 61 mmol, 0.1 equivalent) was added dropwise at −78° C. Stirring was carried out for 5 h at this temperature and then the reaction was warmed to room temperature and stopped. Water (10 mL) was added and the phases were separated. The aqueous phase was extracted with MTBE (2×10 mL) and the combined organic phases were washed successively with 5% NaHCO$_3$ solution (20 mL), saturated NaCl solution (20 mL) and water (20 mL). The extracts were dried with Na$_2$SO$_4$, filtered and the volatile components removed under reduced pressure. A mixture of compounds 1 and 2 (134 mg, 562 μmol, 92%, 13:76% by GC isomer ratio) was obtained as a colourless solid. Compounds 1 and 2 were separated by column chromatography.

Compound 1:

Melting point (mp): T$_m$=51° C.-52° C.

TLC: R$_f$=0.37 (ethyl acetate/cyclohexane, 5:95)

$[\alpha]^{25}_D$=−31.7° (c=0.24 M, EtOH, enantiomer 1a), $[\alpha]^{25}_D$=+33.0° (c=0.49 M, EtOH, enantiomer 1b)

$^1$H-NMR (600 MHz, C$_6$D$_6$) δ=3.98 (d, J=7.0 Hz, 1H, C$_q$(O)C(H)H'O), 3.36 (dd, J=6.9, 1.1 Hz, 1H, C$_q$(O)C(H)H'O), 1.79 (dt, J=12.6, 3.5 Hz, 1H, C$_q$(O)C(H)H'), 1.71 (ddd, J=13.9, 12.5, 3.9 Hz, 1H, C$_q$(O)C(H)H'), 1.66-1.62 (m, 2H, CH$_3$C$_q$CH$_2$), 1.55 (s, 3H, C$_q$CH$_3$), 1.53-1.48 (m, 1H, C$_q$(O)CH), 1.48-1.42 (m, 3H, 2×C$_q$CHC(H)H', CHC(H)H'CH$_2$C$_q$), 1.37 (dtd, J=12.9, 4.8, 2.5 Hz, 1H, CHC(H)H'CH$_2$C$_q$), 0.92 (tt, J=12.2, 3.3 Hz, 1H, C$_q$CH), 0.74 (s, 9H, C(CH$_3$)$_3$), 0.61 (dt, J=13.2, 11.8 Hz, 1H, C$_q$CHC(H)H'), 0.51-0.44 (m, 1H, C$_q$CHC(H)H')

$^{13}$C-NMR (151 MHz, C$_6$D$_6$) δ=107.05 (CH$_3$C$_q$(O)O), 82.84 (C$_q$(O)), 70.78 (C$_q$CH$_2$O), 47.68 (C$_q$CH), 40.65 (C$_q$(O)CH), 36.34 (CH$_3$C$_q$CH$_2$), 35.07 (C(O)C$_q$CH$_2$), 32.15 (C$_q$(CH$_3$)$_3$), 32.03 (C$_q$CHCH$_2$), 27.64 (C(CH$_3$)$_3$), 25.84 (CHCH$_2$CH$_2$C$_q$), 25.41 (C$_q$CHCH$_2$), 24.88 (C$_q$CH$_3$)

IR (GC/FT-IR): ṽ=2944 (s), 2881 (m), 1389 (w) 1259 (w), 1201 (w), 1150 (w), 1038 (m), 859 (w) cm$^{-1}$

MS (EI): m/z=238 [M]$^+$, 57 [(CH$_3$)$_3$C]$^+$

HRMS (ESI-TOF): Calculated for C$_{15}$H$_{26}$O$_2$ [M+H]$^+$ 239.2011; found 239.2010

Odour description: Ambery, ambraketal-like, woody

Compound 2:

TLC: R$_f$=0.37 (ethyl acetate/cyclohexane, 5:95)

$^1$H-NMR (600 MHz, C$_6$D$_6$) δ=3.69 (d, J=6.6 Hz, 1H, C$_q$(O)C(H)H'O), 3.42 (d, J=6.6 Hz, 1H, C$_q$(O)C(H)H'O), 2.08 (ddt, J=13.8, 12.8, 6.4 Hz, 1H, CHC(H)H'CH$_2$C$_q$), 1.70 (dt, J=13.5, 3.3 Hz, 1H, C$_q$(O)C(H)H'), 1.66-1.60 (m, 1H, CH$_3$C$_q$C(H)H'), 1.59-1.56 (m, 1H, C$_q$CHC(H)H'), 1.56-1.51 (m, 2H, C$_q$CHCH$_2$), 1.50 (s, 3H, C$_q$CH$_3$), 1.47 (ddd, J=13.3, 6.4, 1.4 Hz, 1H, CH$_3$C$_q$C(H)H'), 1.30 (dtd, J=12.4, 3.5, 1.4 Hz, 1H, C$_q$CHC(H)H'), 1.16-1.09 (m, 2H, C$_q$(O)C(H)H', CHC(H)H'CH$_2$C$_q$), 1.05 (dddd, J=12.9, 6.6, 3.9, 1.1 Hz, 1H, C$_q$(O)CH), 0.94-0.88 (m, 1H, C$_q$CH), 0.87 (s, 9H, C(CH$_3$)$_3$)

$^{13}$C-NMR (151 MHz, C$_6$D$_6$) δ=108.16 (CH$_3$C$_q$(O)O), 80.60 (C$_q$(O)), 74.74 (C$_q$CH$_2$O), 47.74 (C$_q$CH), 38.24 (C$_q$(O)CH), 33.12 (C(O)C$_q$CH$_2$), 32.12 (C$_q$(CH$_3$)$_3$), 31.85 (CH$_3$C$_q$CH$_2$), 28.87 (C$_q$CHCH$_2$), 27.45 (C(CH$_3$)$_3$), 24.88 (C$_q$CH$_3$), 24.48 (CHCH$_2$CH$_2$C$_q$), 23.35 (C$_q$CHCH$_2$)

IR (GC/FT-IR): ṽ=2944 (s), 2881 (m), 1389 (w) 1201 (w), 1150 (w), 1038 (m), 859 (w) cm$^{-1}$

MS (EI): m/z=238 [M]$^+$, 57 [(CH$_3$)$_3$C]$^+$

Odour description: Woody, cedar wood, slightly animalic

2. Synthesis Route II Towards Compounds of Formula (Ia)

The synthesis steps as described in items 1.1 and 1.2 above were carried out to obtain tert-butyl 3-((1'R,5'R)-5'-(tert-butyl)-2'-methylenecyclohexyl)propanoate (product of the reaction as described in item 1.2 above). Said product was used in the alternative synthetic route as described below to obtain compounds of formula (Ia).

2.1 Synthesis of 3-((1'R,5'R)-5'-(tert-butyl)-2'-methylencyclohexyl)propan-1-ol

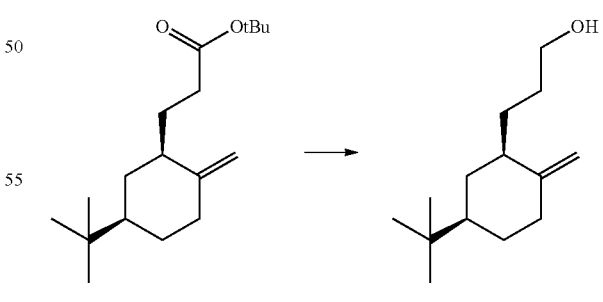

LiAlH$_4$ (164 mg, 4.23 mmol, 1.2 equiv.) was presented in 5 mL THF and cooled to 0° C. The product of the reaction described in item 1.2 above (1.00 g, 3.52 mmol) was dissolved in 5 mL THF and slowly added dropwise while stirring. It was stirred at 0° C. for 1 h, heated to room temperature and ice water (20 mL) was added. The phases were separated and the aqueous phase was extracted with MTBE (3×20 mL). The combined organic extracts were successively washed with 5% NaHCO₃ solution (30 mL), saturated NaCl solution (30 mL) and water (30 mL). Then the extracts were dried with Na₂SO₄, filtered and the volatile components were removed under reduced pressure. The product was is obtained as a colourless liquid (717 mg, 3.41 mmol, 97%, 96:4 isomer mixture (cis/trans)) and used in the next step without further purification.

TLC: R$_f$=0.46 (ethyl acetate/cyclohexane, 20:80)

¹H-NMR (400 MHz, CDCl₃) δ=4.68 (d, J=1.7 Hz, 1H, C=C(H)H'), 4.55 (d, J=1.5 Hz, 1H, C=C(H)H'), 3.67 (t, J=6.2 Hz, 2H, CH₂OH), 2.36 (dt, J=12.9, 3.6 Hz, 1H, CH₂=CC(H)H'), 2.00-1.83 (m, 4H, CH₂=CC(H)H', CH₂=CCH, 2×C$_q$CHC(H)H'), 1.78-1.62 (m, 3H, CHC(H)H'CH₂), 1.35-1.20 (m, 2H, CHC(H)H'CH₂, C$_q$CH), 1.05 (qd, J=12.4, 3.8 Hz, 1H, C$_q$CHC(H)H'), 0.85 (s, 9H, C(CH₃)₃), 0.73 (q, J=12.0 Hz, 1H, C$_q$CHC(H)H')

¹³C-NMR (101 MHz, CDCl₃) δ=153.33 (C=CH₂), 103.76 (C=CH₂), 63.44 (CH₂OH), 48.16 (C$_q$CH), 42.35 (CH₂=CCH), 37.11 (CH₂=CCH₂), 35.65 (C$_q$CHCH₂), 32.47 (C(CH₃)₃), 30.64 (CH₂CH₂OH), 29.70 (C$_q$CHCH₂), 28.65 (CHCH₂CH₂), 27.66 (C(CH₃)₃)

IR (GC/FT-IR): ṽ=3689 (w), 3089 (w), 2949 (s), 2875 (w), 1371 (w), 1054 (w) 892 (w) cm⁻¹

MS (EI): m/z=210 [M]⁺, 57 [(CH₃)₃C]⁺

HRMS (ESI-TOF): Calculated for C14H26O [M+H]⁺ 211.2062; found 211.2053

2.2 Synthesis of 3-((1'R,5'R)-5'-(tert-butyl)-2'-methylencyclohexyl)propanal

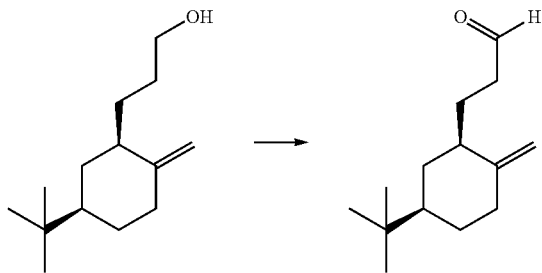

The product of the reaction described in item 2.1 above (2.10 g, 9.73 mmol) was dissolved in 25 mL CH₂Cl₂. Dess-Martin periodinane (4.95 g, 11.68 mmol, 1.2 equiv.) was added and the reaction mixture was stirred for 4 h at room temperature. It was diluted with Et₂O (50 mL) and 5% NaOH solution (10 mL) was added. The phases were separated and the aqueous phase was extracted with Et₂O (10 mL). The combined organic extracts were washed with saturated NaCl solution (50 mL) and water (50 mL). They were dried with Na₂SO₄, filtered and the volatile components removed under reduced pressure. The raw product was purified by column chromatography (100 mL SiO₂, 3-5% EtOAc in cyclohexane). The product was obtained as a colorless liquid (1.84 g, 8.86 mmol, 91%, 97:3 mixture of isomers (cis/trans)).

TLC: R$_f$=0.49 (ethyl acetate/cyclohexane, 5:95)

¹H-NMR (400 MHz, CDCl₃) δ=9.80 (dd, J=1.7 Hz, 1H, CHO), 4.71 (d, J=1.6 Hz, 1H, C=C(H)H'), 4.54 (d, J=1.5 Hz, 1H, C=C(H)H'), 2.57-2.50 (m, 2H, CH₂CHO), 2.37 (ddd, J=12.8, 4.0, 2.8 Hz, 1H, CH₂=CC(H)H'), 2.02-1.92 (m, 2H, CH₂=CC(H)H', CHC(H)H'CH₂), 1.91-1.84 (m, 3H, CH₂=CCH, 2×C$_q$CHC(H)H'), 1.67-1.56 (m, 1H, CHC(H)H'CH₂), 1.24 (tt, J=12.1, 3.1 Hz, 1H, C$_q$CH), 1.06 (qd, J=12.6, 4.0 Hz, 1H, C$_q$CHC(H)H'), 0.85 (s, 9H, C(CH₃)₃), 0.76 (q, J=12.9 Hz, 1H, C$_q$CHC(H)H')

¹³C-NMR (101 MHz, CDCl₃) δ=202.74 (CHO), 152.40 (C=CH₂), 104.08 (C=CH₂), 48.07 (C$_q$CH), 42.01 (CH₂=CCH, CH₂CHO), 36.98 (CH₂=CCH₂), 35.61 (C$_q$CHCH₂), 32.45 (C(CH₃)₃), 29.62 (C$_q$CHCH₂), 27.63 (C(CH₃)₃), 24.63 (CHCH₂CH₂)

IR (GC/FT-IR): ṽ=3089 (w), 2952 (s), 2873 (w), 2711 (w) 1742 (m) 1370 (w), 893 (w) cm⁻¹

MS (EI): m/z=208 [M]⁺, 57 [(CH₃)₃C]⁺, [CH₂CH₂COH]⁺

Odour description: Bourgeonal, floral, lily of the valley, cucumber, very strong, bit fruity melon 2.3 Synthesis of 4-((1'R,5'R,2R/S)-5'-(tert-butyl)-2'-methylencyclohexyl)butan-2-ol

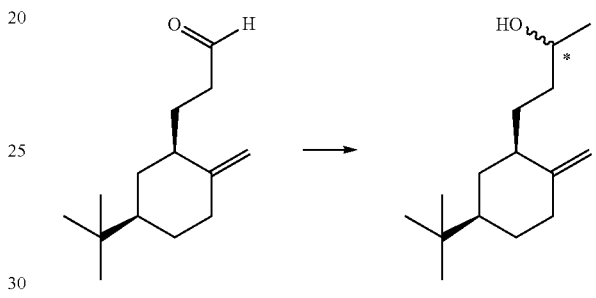

The product of the reaction described in item 2.2 above (315 mg, 1.29 mmol) was dissolved in 5 mL THF and cooled to −78° C. At this temperature, MeLi (1.61 mL, 1.6 M solution in Et₂O, 2.57 mmol, 2 equiv.) was slowly added dropwise and it was stirred for 4 h. It was heated to room temperature and water (5 mL) was added. The phases were separated and the aqueous phase was extracted with Et₂O (3×5 mL). The combined organic extracts were dried with Na₂SO₄ and filtered. The volatile components were removed under reduced pressure and the raw product was purified by column chromatography (100 mL SiO₂, 10% EtOAc in cyclohexane). The product was obtained as a colorless liquid (259 mg, 1.15 mmol, 90%, 96:4 isomer mixture (cis/trans)). Both isomers also consisted of a 1:1 mixture of isomers through the stereogenic carbon atom with the secondary hydroxyl group, which was not identifiable by gas chromatography, but by NMR spectroscopy.

TLC: R$_f$=0.21 (ethyl acetate/cyclohexane, 10:90)

¹H-NMR (400 MHz, CDCl₃) δ=4.68 (d, J=1.7 Hz, 1H, C=C(H)H'), 4.56 (d, J=1.4 Hz, 1H, C=C(H)H'), 3.88-3.76 (m, 1H, CH(OH)CH₃), 2.36 (dt, J=12.8, 3.1 Hz, 1H, CH₂=CC(H)H'), 2.02-1.90 (m, 2H, CH₂=CC(H)H', C$_q$CHC(H)H'), 1.89-1.80 (m, 1H, CH₂=CCH, C$_q$CHC(H)H'), 1.78-1.66 (m, 1H, CHC(H)H'CH₂), 1.59-1.45 (m, 1H, CH₂C(H)OH), 1.43-1.36 (m, 1H, C$_q$CH), 1.23 (d, J=2.2 Hz, 3H/2, CH(OH)CH₃ (1st isomer)), 1.21 (d, J=2.3 Hz, 3H/2 CH(OH)CH₃ (2nd isomer)), 1.05 (qd, J=12.5, 4.0 Hz, 1H, C$_q$CHC(H)H'), 0.85 (s, 9H, C(CH₃)₃), 0.73 (qd, J=12.0, 1.8 Hz, 1H, C$_q$CHC(H)H')

¹³C-NMR (101 MHz, CDCl₃) δ=153.39 (a-C=CH₂), 153.29 (b-C=CH₂), 103.79 (a-C=CH₂), 103.75 (b-C=CH₂), 68.64 (a-CH(OH)CH₃), 68.62 (b-CH(OH) CH₃), 48.18 (C$_q$CH), 42.61 (a-CH₂=CCH), 42.59 (b-CH₂=CCH), 37.14 (a-CH₂=CCH₂, a-CH₂C(H)OH), 37.12 (b-CH₂=CCH₂, b-CH₂C(H)OH), 35.76 (a-C$_q$CHCH₂), 35.68 (b-C$_q$CHCH₂), 32.46 (C(CH₃)₃), 29.72 (C$_q$CHCH$_2$), 28.72 (a-CHCH$_2$CH$_2$), 28.64 (b-CHCH$_2$CH$_2$), 27.66 (C(CH$_3$)$_3$), 23.61 (a-CH(OH)CH$_3$), 23.50 (b-CH(OH)CH$_3$)

IR (GC/FT-IR): $\tilde{v}$=3655 (w), 3089 (w), 2950 (s), 2878 (w), 1371 (w), 892 (w) cm$^{-1}$ MS (EI): m/z=224 [M]$^+$, 167 [M–(CH$_3$)$_3$C]$^+$, 57 [(CH$_3$)$_3$C]$^+$ HRMS (ESI-TOF): Calculated for C$_{15}$H$_{28}$O [M+H]$^+$ 225.2218; found 225.2210

2.4 Synthesis of 4-((1'R,5'R)-5'-(tert-butyl)-2'-methylencyclohexyl)butan-2-one

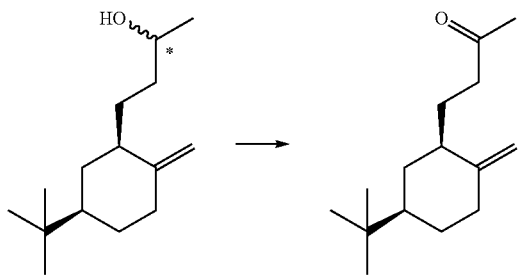 [SMILES: C=C1CC[C@@H](C(C)(C)C)C[C@H]1CCC(C)O ; C=C1CC[C@@H](C(C)(C)C)C[C@H]1CCC(C)=O]

The product of the reaction described in item 2.3 above (145 mg, 630 µmol) was dissolved in 4 mL CH$_2$Cl$_2$. Dess-Martin periodinane (321 mg, 756 µmol, 1.2 equiv.) was added to the solution and stirred for 3 h at room temperature. The reaction mixture was diluted with Et$_2$O (10 mL) and 5% NaOH solution (4 mL) was added. The phases were separated and the aqueous phase extracted with Et$_2$O (5 mL). The combined organic phases were washed successively with saturated NaCl solution (10 mL) and water (10 mL). The extracts were dried with Na$_2$SO$_4$, filtered and the volatile components removed under reduced pressure. The raw product was purified by column chromatography (50 mL SiO$_2$, 4-5% EtOAc in cyclohexane) and the product was obtained as a colorless liquid (116 mg, 553 µmol, 83%, 95:5 isomer mixture (cis/trans)). The analytical data of the obtained product correspond to those presented in item 1.4 above.

In order to obtain the compounds of formula (Ia), the reaction steps as described in items 1.5 and 1.6 above were carried out.

3. Synthesis Route Towards Compounds of Formula (Ib)

3.1 Synthesis of 3-methylbut-3-en-1-yl-4-methylbenzenesulfonate

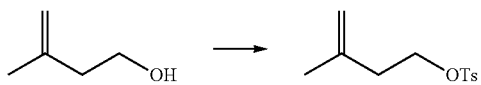

The alcohol (10 mL, 98.7 mmol) was dissolved in 50 mL pyridine and cooled to 0° C. At this temperature, p-toluenesulfonyl chloride (TsCl, 21.8 g, 113.5 mmol, 1.15 equiv.) was added in small portions and stirred for 2.5 h at this temperature. It was warmed to room temperature and the reaction was terminated with 2M HCl solution (100 mL). The phases were separated and the aqueous phase was extracted with MTBE (2×100 mL). The combined organic phases were successively washed with 10% NH$_4$Cl solution (100 mL), 5% NaHCO$_3$ solution (100 mL) and saturated NaCl solution (100 mL). The organic phases were dried with Na$_2$SO$_4$, filtered and the volatile components were removed under reduced pressure. The product was obtained as a colorless liquid (21.2 g, 88.2 mmol, 89%) and carried over to the next step without any purification.

TLC: R$_f$=0.49 (ethyl acetate/cyclohexane, 20:80)
GC: DB-1 column: t$_R$=13.4 min
$^1$H-NMR (400 MHz, CDCl$_3$) δ=7.79 (d, J=8.3 Hz, 2H, 2×ArH), 7.35 (d, J=8.1 Hz, 1H, 2×ArH), 4.79 (s, 1H, C=C(H)H'), 4.68 (s, 1H, C=C(H)H'), 4.13 (t, J=6.9 Hz, 2H, CH$_2$OTs), 2.45 (s, 3H, ArCH$_3$), 2.35 (t, J=6.8 Hz, 2H, C(=CH$_2$)CH$_2$), 1.66 (s, 3H, C(=CH$_2$)CH$_3$)
$^{13}$C-NMR (101 MHz, CDCl$_3$) δ=144.73 (CH$_3$C(Ar)), 140.13 (C=CH$_2$), 133.16 (SO$_2$C(Ar)), 129.81 (2×Ar), 127.91 (2×Ar), 113.10 (C=CH$_2$), 68.54 (CH$_2$OTs), 36.76 (C(=CH$_2$)CH$_2$), 22.34 C(=CH$_2$)CH$_3$), 21.65 (ArCH$_3$)
IR (GC/FT-IR): $\tilde{v}$=3084 (w), 2968 (m), 2937 (w), 1392 (m) 1188 (s), 1088 (m), 1025 (s), 973 (m) cm$^{-1}$
MS (EI): m/z=155 [Ts]$^+$, 91 [(C$_6$H$_4$)CH$_3$]$^+$, 55 [(CH$_3$)C(=CH$_2$)CH$_2$]$^+$ 3.2 Synthesis of 4-iodo-2-methylbut-1-ene

NaI (53.2 g, 351 mmol, 4 equiv.) was dissolved in 300 mL acetone. The product of the reaction described in item 3.1 above (21.2 g, 87.8 mmol) was added dropwise at room temperature and stirred for 24 h at this temperature. Water (125 mL) was added and the product was extracted with hexane (3×100 mL). The combined organic phases were washed successively with water (100 mL) and saturated NaCl solution (100 mL). The organic phases were dried with Na$_2$SO$_4$, filtered and the volatile components removed under reduced pressure. The product was obtained as a slightly yellow liquid (10.9 g, 55.3 mmol, 63%) and carried over to the next step without any further purification.

$^1$H-NMR (400 MHz, CDCl$_3$) δ=4.86 (d, J=0.8 Hz, 1H, C=C(H)H'), 4.76 (d, J=1.0 Hz, 1H, C=C(H)H'), 3.26 (t, J=7.6 Hz, 2H, CH$_{21}$), 2.59 (t, J=7.5 Hz, 2H, C(=CH$_2$)CH$_2$), 1.74 (t, J=1.1 Hz, 3H, C(=CH$_2$)CH$_3$)
$^{13}$C-NMR (101 MHz, CDCl$_3$) δ=143.90 (C=CH$_2$), 112.29 (C=CH$_2$), 41.88 (C(=CH$_2$)CH$_2$), 21.68 C(=CH$_2$)CH$_3$), 3.52 (CH$_{21}$)
IR (GC/FT-IR): $\tilde{v}$=3086 (m), 2983 (s), 2943 (m), 1851 (m), 1447 (m), 1239 (s), 1171 (s), 899 (s) cm$^{-1}$
MS (EI): m/z=196 [M]$^+$, 127 [1]$^+$, 69 [(CH$_3$)C(=CH$_2$)CH$_2$CH$_2$]$^+$, 41 [CH$_3$C=CH$_2$]$^+$ 3.3 Synthesis of (2R,4R)-4-(tert-butyl)-2-(3'-methylbut-3'-en-1'-yl)cyclohexan-1-one

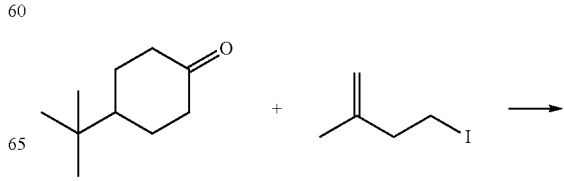

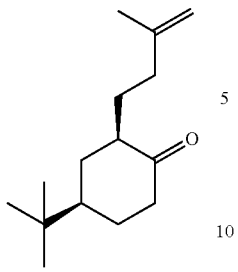

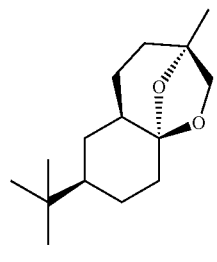

3 + 4

Tert-butylcyclohexanone (4.92 g, 31.6 mmol, 1.25 equiv.) was dissolved in 50 mL toluene, KOtBu (3.40 g, 30.3 mmol, 1.2 equivalent) was added and stirred for 1 h at room temperature. The product of the reaction described in item 3.2 above (5.00 g, 25.3 mmol) was added to the solution dropwise and it was stirred at room temperature for 4 days. 10% NH$_4$Cl solution (50 mL) was added and the phases were separated. The aqueous phase was extracted with MTBE (3×50 mL) and the combined organic phases were washed with saturated NaCl solution (100 mL). After drying with Na$_2$SO$_4$, it was filtered and the volatile components were removed under reduced pressure. The raw product was purified by Kugelrohr distillation (1.0 mbar, 120° C. to 1.2 mbar, 178° C.) and then by column chromatography (100 mL SiO$_2$, 5% EtOAc in cyclohexane). The product was obtained as a colourless liquid (557 mg, 2.51 mmol, 10%, 8:1 mixture of isomers (cis/trans)).

TLC: R$_f$=0.49 (ethyl acetate/cyclohexane, 5:95)

$^1$H-NMR (600 MHz, CDCl$_3$) δ=4.69 (ddt, J=20.8, 2.4, 1.4 Hz, 2H, C=CH$_2$), 2.41-2.36 (m, 1H, C(=O)C(H)H'), 2.33 (ddd, J=13.5, 5.9, 1.3 Hz, 1H, C(=O)C(H)H'), 2.31-2.24 (m, 1H, C(=O)CH), 2.15 (ddt, J=12.9, 5.2, 3.3 Hz, 1H, C$_q$CHC(H)H'CH), 2.09 (ddt, J=12.8, 5.9, 3.0 Hz, 1H, C$_q$CHC(H)H'CH$_2$), 2.07-1.95 (m, 3H, C(=O)CHC(H)H'CH$_2$C$_q$), 1.72 (t, J=1.2 Hz, 3H, C(=CH$_2$)CH$_3$), 1.58 (tt, J=12.2, 3.2 Hz, 1H, C$_q$CH), 1.44 (qdd, J=12.1, 4.6, 1.2 Hz, 1H, C$_q$CHC(H)H'CH$_2$), 1.30-1.22 (m, 1H, C$_q$CHC(H)H'), 1.17-1.10 (m, 1H, C$_q$CHC(H)H'CH), 0.92 (d, J=1.2 Hz, 9H, C(CH$_3$)$_3$)

$^{13}$C-NMR (151 MHz, CDCl$_3$) δ=213.47 (C=O), 145.78 (C=CH$_2$), 110.02 (C=CH$_2$), 49.02 (C(=O)CH), 47.19 (C$_q$CH), 41.76 (C(=O)CH$_2$), 35.21 (CH$_2$C=CH$_2$), 35.12 (C$_q$CHCH$_2$CH), 32.48 (C(CH$_3$)$_3$), 28.80 (C$_q$CHCH$_2$CH$_2$), 27.67 (C(CH$_3$)$_3$), 27.09 (C(=O)CHCH$_2$), 22.35 (C(=CH$_2$)CH$_3$)

IR (GC/FT-IR): ṽ=3080 (w), 2967 (s), 2877 (w), 1728 (s), 1453 (w), 1223 (w), 891 (w) cm$^{-1}$

MS (EI): m/z=222 [M]$^+$, [(CH$_3$)$_3$C]$^+$

HRMS (ESI-TOF): Calculated for C$_{15}$H$_{26}$O [M+H]$^+$ 223.2062; found 223.2055

3.4 Synthesis of Compounds 3 and 4

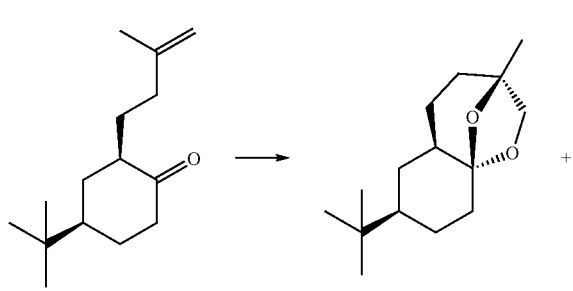

The product of the reaction described in item 3.3 above (52 mg, 213 μmol) was dissolved in 1.5 mL each of EtOAc and MeCN. The solution was stirred at room temperature and a solution of RuCl3·3 H$_2$O (4 mg, 21 μmol, 0.1 equiv.) and NaIO$_4$ (70 mg, 320 μmol, 1.5 equiv.) in 0.7 mL H$_2$O was slowly added dropwise. It was stirred for 10 min at room temperature and then 10% Na$_2$S$_2$O$_3$ solution (5 mL) was added. The phases were separated and the aqueous phase extracted with EtOAc (3×5 mL). The combined organic extracts were washed with water (20 mL), dried with Na$_2$SO$_4$ and filtered. The volatile components were removed under reduced pressure and the raw product was purified by preparative gas chromatography to obtain compound 3 (30%) and compound 4 (32%).

First Stereoisomer (Compound 3):

TLC: R$_f$=0.41 (ethyl acetate/cyclohexane, 5:95)

$^1$H-NMR (600 MHz, C$_6$D$_6$) δ=3.68 (d, J=6.7 Hz, 1H, C$_q$C(H)H'O), 3.39 (dd, J=6.7, 1.9 Hz, 1H, C$_q$C(H)H'O), 2.10-2.02 (m, 2H, OC$_q$(O)C(H)H', C$_q$CHC(H)H'), 1.73 (ddd, J=13.7, 13.0, 4.5 Hz, 1H, OC$_q$(O)C(H)H'), 1.65-1.59 (m, 2H, C$_q$CHC(H)H'CH$_2$, CH$_3$C$_q$C(H)H'), 1.56-1.49 (m, 3H, C$_q$CHC(H)H'CH, OC$_q$(O)CH, C$_q$CHC(H)H'CH$_2$), 1.43-1.38 (m, 1H, C$_q$CHC(H)H'CH), 1.15 (ddd, J=13.7, 5.8, 1.4 Hz, 1H, C$_q$CHC(H)H'), 1.10 (s, 3H, CH$_3$C$_q$), 1.04 (ddd, J=13.4, 6.3, 1.5 Hz, 1H, CH$_3$C$_q$C(H)H'), 1.01-0.96 (m, 1H, C$_q$CH), 0.84 (s, 9H, C(CH$_3$)$_3$)

$^{13}$C-NMR (151 MHz, C$_6$D$_6$) δ=109.21 (C$_q$(O)O), 79.87 (CH$_3$C$_q$O), 73.31 (C$_q$CH$_2$O), 47.85 (C$_q$CH), 40.48 (OC$_q$(O)CH), 35.94 (OC$_q$(O)CH$_2$), 32.36 (C(CH$_3$)$_3$), 31.46 (CH$_3$C$_q$CH$_2$), 31.14 (C$_q$CHCH$_2$CH), 27.90 (C(CH$_3$)$_3$), 25.19 (C$_q$CHCH$_2$CH$_2$), 24.55 C$_q$CHCH$_2$CH$_2$C$_q$CH$_3$), 23.39 (C$_q$CH$_3$)

IR (GC/FT-IR): ṽ=2947 (s), 2885 (m), 1370 (w), 1325 (w), 1114 (w), 1062 (m) cm$^{-1}$

MS (EI): m/z=238 [M]$^+$, 210 [M–CH$_2$CH$_2$]$^+$, 208 [M–CH$_2$O]$^+$, 181 [M–[(CH$_3$)$_3$C]$^+$, 57 [(CH$_3$)$_3$C]$^+$

Odour description: Ambery, woody

Second Stereoisomer (Compound 4):

TLC: R$_f$=0.39 (ethyl acetate/cyclohexane, 5:95)

$^1$H-NMR (600 MHz, C$_6$D$_6$) δ=3.62 (d, J=6.7 Hz, 1H, C$_q$C(H)H'O), 3.36 (dd, J=6.7, 2.0 Hz, 1H, C$_q$C(H)H'O), 2.07 (dt, J=12.9, 3.4 Hz, 1H, OC$_q$(O)C(H)H'), 1.75 (td, J=13.4, 4.4 Hz, 1H, OC$_q$(O)C(H)H'), 1.66-1.61 (m, 1H, C$_q$CHC(H)H'CH$_2$), 1.60-1.53 (m, 1H, CH$_3$C$_q$C(H)H'), 1.53-1.47 (m, 3H, C$_q$CHC(H)H'CH, C$_q$CHC(H)H'CH$_2$, OC$_q$(O)CH), 1.44-1.31 (m, 2H, OC$_q$(O)CHCH$_2$), 1.24-1.19 (m, 1H, C$_q$CHC(H)H'CH), 1.13 (s, 1H, CH$_3$C$_q$), 0.99 (tt, J=12.2, 2.9 Hz, 1H, C$_q$CH), 0.84 (s, 9H, C(CH$_3$)$_3$)

$^{13}$C-NMR (151 MHz, C$_6$D$_6$) δ=108.61 (C$_q$(O)O), 79.02 (CH$_3$C$_q$O), 73.95 (C$_q$CH$_2$O), 47.54 (C$_q$CH), 41.84 (OC$_q$(O)CH), 35.44 (OC$_q$(O)CH$_2$), 35.24 (CH$_3$C$_q$CH$_2$), 32.35 (C(CH$_3$)$_3$), 32.16 (C$_q$CHCH$_2$CH), 27.79 (C(CH$_3$)$_3$), 25.97 (C$_q$CHCH$_2$CH$_2$C$_q$CH$_3$), 24.85 (C$_q$CHCH$_2$CH$_2$), 22.93 (C$_q$CH$_3$)

IR (GC/FT-IR): ṽ=2942 (s), 2885 (m), 1374 (w), 1233 (w), 1138 (w), 1031 (w) cm$^{-1}$

MS (EI): m/z=238 [M]$^+$, 210 [M–CH$_2$CH$_2$]$^+$, 208 [M–CH$_2$O]$^+$, 181 [M–[(CH$_3$)$_3$C]$^+$, 57 [(CH$_3$)$_3$C]$^+$

Odour description: Woody, ambergris-like

4. Perfume Oils

The numerical values indicated in Table 2 and Table 3 below relate to the weight, respectively.

Perfume Oil 1

TABLE 2

(Middle column) Content of components of perfume oil 1; (right column) content of components of perfume oil 1 with compound 1, or with compound 2 or with mixture of compounds 3 + 4 (1:1 weight ratio of compound 3 to compound 4) according to the invention.

| | | |
|---|---|---|
| AMBERWOOD ® F | 7.000 | 7.000 |
| AMBRETTOLIDE | 6.000 | 6.000 |
| Compound 1 or 2, or mixture 3 + 4 | 0.000 | 34.000 |
| BHT IONOL | 3.000 | 3.000 |
| CASSIS BASE 345 BB | 10.000 | 10.000 |
| CITRONELLOL 950 | 10.000 | 10.000 |
| CITRONELLYL ACETATE EXTRA | 1.000 | 1.000 |
| DAMASCENONE 10% DPG | 5.000 | 5.000 |
| DAMASCONE ALPHA 10% DPG | 1.000 | 1.000 |
| DIPROPYLENE GLYCOL | 209.000 | 175.000 |
| ETHYLENE BRASSYLATE | 325.000 | 325.000 |
| GERANIOL SUPER | 20.000 | 20.000 |
| GERANYL ACETATE PURE | 1.000 | 1.000 |
| HEDIONE | 120.000 | 120.000 |
| HEDIONE HC/30 | 30.000 | 30.000 |
| HELIONAL | 4.000 | 4.000 |
| HEXENYL ACETATE CIS TRANS-3 10% DPG | 3.000 | 3.000 |
| HEXYL CINNAMIC ALDEHYDE ALPHA | 20.000 | 20.000 |
| HYDROXY CITRONELLAL | 15.000 | 15.000 |
| INDOLE FF 10% DPG | 1.000 | 1.000 |
| IONONE BETA | 8.000 | 8.000 |
| ISO E SUPER | 100.000 | 100.000 |
| LEMON OIL WINTER BERGAPTEN FREE | 10.000 | 10.000 |
| LINALOOL | 5.000 | 5.000 |
| LINALYL ACETATE | 25.000 | 25.000 |
| MAGNOLAN | 20.000 | 20.000 |
| MANDARIN OIL DIST. DECOL. | 5.000 | 5.000 |
| METHYL IONONE GAMMA PURE/IFF | 1.000 | 1.000 |
| METHYL OCTIN CARBONATE 1% DPG | 5.000 | 5.000 |
| NEROL 900 | 2.000 | 2.000 |
| PHENYLETHYL ALCOHOL | 20.000 | 20.000 |
| ROSESSENCE 193E | 3.000 | 3.000 |
| VERTOCITRAL 10% DPG | 5.000 | 5.000 |

After the addition of compound 1, or of compound 2, or of a mixture of compounds 3+4 to perfume oil 1 as listed above (cf. Table 2, middle column), the obtained perfume oil (cf. Table 2, right column) smells more harmonious, more flowery and more natural.

Perfume Oil 2

TABLE 3

(Middle column) Content of components of perfume oil 2; (right column) content of components of perfume oil 2 with compound 1, or with compound 2 or with mixture of compounds 3 + 4 (1:1 weight ratio of compound 3 to compound 4) according to the invention.

| | | |
|---|---|---|
| AMBRETTOLIDE | 15.000 | 15.000 |
| Compound 1 or 2, or mixture 3 + 4 | 0.000 | 40.000 |
| BASIL OIL COMORES TYPE E 10% DPG | 2.000 | 2.000 |
| BERGAMOT OIL | 40.000 | 40.000 |
| BOURGEONAL 10% DPG | 5.000 | 5.000 |
| CARDAMOM OIL | 2.000 | 2.000 |

TABLE 3-continued (Middle column) Content of components of perfume oil 2; (right column) content of components of perfume oil 2 with compound 1, or with compound 2 or with mixture of compounds 3 + 4 (1:1 weight ratio of compound 3 to compound 4) according to the invention.

| | | |
|---|---|---|
| CASHMERAN | 15.000 | 15.000 |
| CINNAMON BARK OIL CEYLON 10% DPG | 5.000 | 5.000 |
| CLARY SAGE OIL | 2.000 | 2.000 |
| CORIANDER OIL | 3.000 | 3.000 |
| COUMARIN | 16.000 | 16.000 |
| DAMASCENONE | 2.000 | 2.000 |
| DIHYDRO MYRCENOL | 2.000 | 2.000 |
| DIPROPYLENE GLYCOL | 52.000 | 12.000 |
| FIR BALSAM ABS. 10% DPG | 5.000 | 5.000 |
| FLOROSA | 5.000 | 5.000 |
| GALAXOLIDE 50% IN DPG | 150.000 | 150.000 |
| GERANIOL SUPER | 3.000 | 3.000 |
| GERANYL ACETATE 60 | 2.000 | 2.000 |
| GLOBALIDE ® | 210.000 | 210.000 |
| GUAIAC WOOD OIL | 5.000 | 5.000 |
| HEDIONE | 30.000 | 30.000 |
| HEDIONE HC/30 | 60.000 | 60.000 |
| HEXENOL CIS-3 10% DPG | 5.000 | 5.000 |
| ISO E SUPER | 130.000 | 130.000 |
| ISOBUTYL QUINOLINE DL 100% 1% DPG | 5.000 | 5.000 |
| JAVANOL | 3.000 | 3.000 |
| LAVANDINOIL ABRIALIS NAT. | 3.000 | 3.000 |
| LEMON OIL WINTER ITALIE | 15.000 | 15.000 |
| LINALOOL | 15.000 | 15.000 |
| LINALYL ACETATE | 25.000 | 25.000 |
| METHYL IONONE GAMMA PURE/IFF | 3.000 | 3.000 |
| MUSCENONE | 4.000 | 4.000 |
| PATCHOULI OIL DECOL. | 5.000 | 5.000 |
| SANDALWOOD OIL EAST IND. 10% DPG | 5.000 | 5.000 |
| SANDRANOL ® | 10.000 | 10.000 |
| TONALIDE | 130.000 | 130.000 |
| VANILLIN | 3.000 | 3.000 |
| VERTOCITRAL 10% DPG | 5.000 | 5.000 |
| VETIVER OIL HAITI | 3.000 | 3.000 |

After the addition of compound 1, or of compound 2, or of a mixture of compounds 3+4 to perfume oil 2 as listed above (cf. Table 3, middle column), the obtained perfume oil (cf. Table 3, right column) has more radiance and appears more rounded and more harmonious.

The invention claimed is:

1. A compound of formula (I)

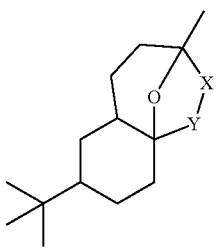

(I)

wherein X and Y are selected from the group consisting of —O— and —CH$_2$—, respectively, and when X is —O—, then Y is —CH$_2$—, and when X is —CH$_2$—, then Y is —O—.

2. A composition comprising one, two, three or more compound(s) of formula (I).

3. A method for producing a compound according to claim 1 or a composition comprising the compound, the method comprising one or more of the following reaction steps:

(i)
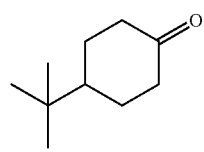 + 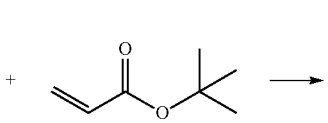 →
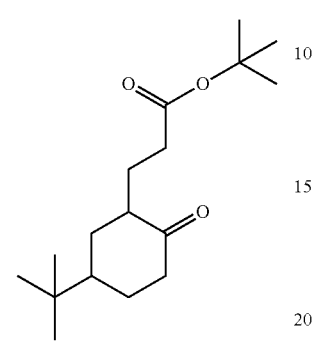
(ii)
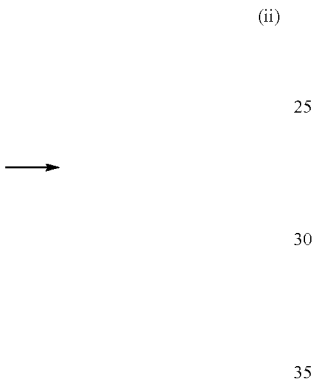 →
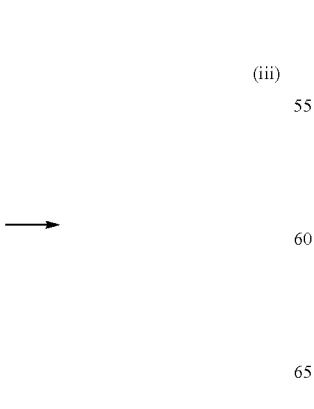 →
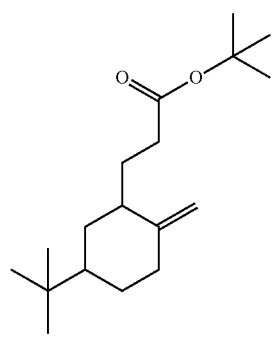 →
-continued
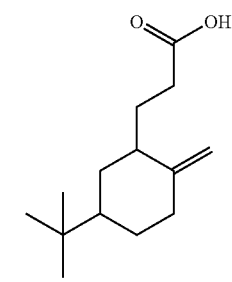
(iv)
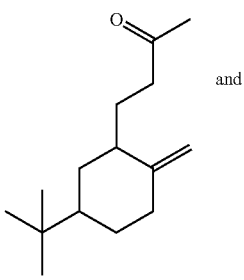 → 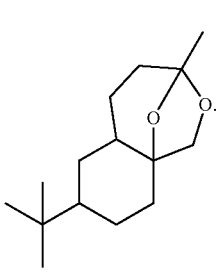 and
(v)
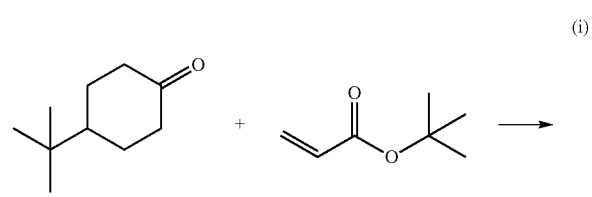
(Ia)
4. A method for producing a compound according to claim 1 or a composition comprising the compound, the method comprising one or more of the following reaction steps:
(i)

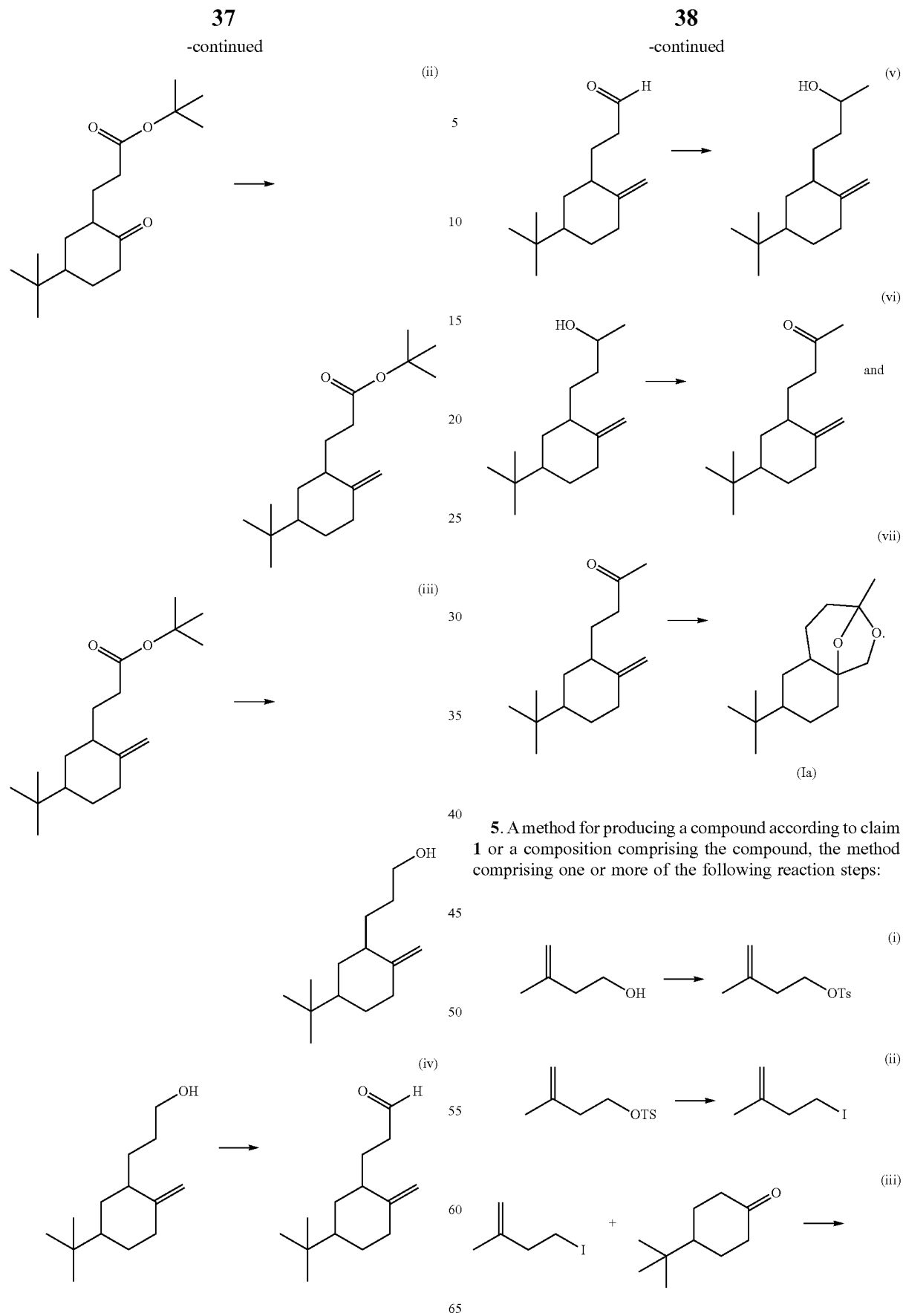
5. A method for producing a compound according to claim 1 or a composition comprising the compound, the method comprising one or more of the following reaction steps:

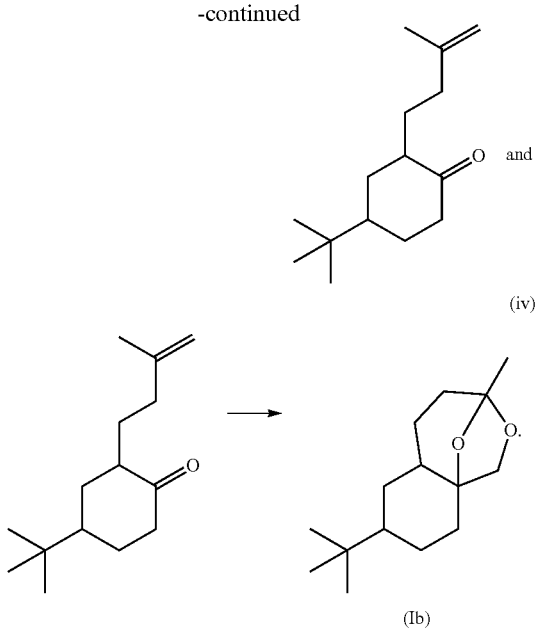

6. A fragrance substance composition comprising:
(i) a compound according to claim 1, or
(ii) a composition comprising the compound and one or more additional fragrance substances.

7. A perfumed product comprising a compound according to claim 1 or a composition comprising the compound, or a fragrance substance composition comprising the compound or the composition.

8. The perfumed product according to claim 7, wherein the product is selected from the group consisting of detergents and cleaning agents, hygiene or care products, preferably in the field of body and hair care, cosmetics and household, preferably from the group consisting of perfume extracts, eau de parfums, eau de toilettes, aftershave lotions, eau de colognes, pre-shave products, splash colognes, perfumed refreshing wipes, acidic, alkaline or neutral detergents, textile fresheners, ironing aids, liquid detergents, powder detergents, laundry pre-treatments, fabric softeners, washing soaps, washing tablets, disinfectants, surface disinfectants, air fresheners, aerosol sprays, waxes and polishes, body care products, hand creams and lotions, foot creams and lotions, depilatory creams and lotions, aftershave creams and lotions, tanning creams and lotions, hair care products, deodorants, antiperspirants, decorative cosmetic products, candles, lamp oils, incense sticks, insecticides, repellents, and fuels.

9. The perfumed product according to claim 7, wherein the one or more compound(s) of formula (I) is/are contained in a sensorially effective amount.

10. A method for producing a perfumed product comprising:
(i) providing a compound according to claim 1 or a composition comprising the compound, or a fragrance substance composition comprising the compound or the composition,
(ii) providing one or more further components of the perfumed product to be produced, and
(iii) contacting or mixing the further components provided in (ii) with a sensorially effective amount of the components provided in (i).

11. A method for perfuming a product comprising:
(a) providing
(i) a compound according to claim 1,
(ii) a composition comprising the compound, or
(iii) a fragrance substance composition comprising the compound or the composition, and
(b) adding (i), (ii), or (iii) to a product to be perfumed in a sensorially effective amount.

12. A method for perfuming hair, skin, textile fibres, surfaces and/or ambient air comprising:
(a) providing
(i) a compound according to claim 1,
(ii) a composition comprising the compound,
(iii) a fragrance substance composition comprising the compound, or
(iv) a perfumed product comprising the compound, the composition, or the fragrance substance composition, and
(b) applying or introducing (i), (ii), (iii), or (iv) to the hair, skin, textile fibres, surfaces and/or ambient air in a sensorially effective amount to the hair or skin or fibres or surface to be perfumed, or into the ambient air to be perfumed, in a sensorially effective amount.

* * * * *